(12) United States Patent
Shelton, IV et al.

(10) Patent No.: US 7,434,717 B2
(45) Date of Patent: Oct. 14, 2008

(54) APPARATUS FOR CLOSING A CURVED ANVIL OF A SURGICAL STAPLING DEVICE

(75) Inventors: Frederick E. Shelton, IV, New Vienna, OH (US); Jerome R. Morgan, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 11/652,188

(22) Filed: Jan. 11, 2007

(65) Prior Publication Data

US 2008/0169327 A1 Jul. 17, 2008

(51) Int. Cl.
*A61B 17/068* (2006.01)
(52) U.S. Cl. .................... 227/176.1; 227/19; 227/175.1
(58) Field of Classification Search .................. 227/19, 227/175.1, 176.1, 178.1, 180.1
See application file for complete search history.

(56) References Cited

U.S. PATENT DOCUMENTS

| | | | |
|---|---|---|---|
| 3,551,987 A | 1/1971 | Wilkinson | |
| 3,643,851 A | 2/1972 | Green et al. | |
| 3,662,939 A | 5/1972 | Bryan | |
| 3,717,294 A | 2/1973 | Green | |
| 3,819,100 A | 6/1974 | Noiles et al. | |
| 4,331,277 A | 5/1982 | Green | |
| 4,383,634 A | 5/1983 | Green | |
| 4,402,445 A | 9/1983 | Green | |
| 4,415,112 A | 11/1983 | Green | |
| 4,475,679 A | 10/1984 | Fleury, Jr. | |
| 4,500,024 A | 2/1985 | DiGiovanni et al. | |
| 4,522,327 A | 6/1985 | Korthoff et al. | |
| 4,530,453 A | 7/1985 | Green | |
| 4,566,620 A | 1/1986 | Green et al. | |
| 4,573,622 A | 3/1986 | Green et al. | |
| 4,580,712 A | 4/1986 | Green | |
| 4,610,383 A | 9/1986 | Rothfuss et al. | |
| 4,629,107 A | 12/1986 | Fedotov et al. | |
| 4,671,445 A | 6/1987 | Barker et al. | |
| 4,715,520 A | 12/1987 | Roehr, Jr. et al. | |

(Continued)

FOREIGN PATENT DOCUMENTS

CA 2458946 A1 3/2003

(Continued)

OTHER PUBLICATIONS

U.S. Appl. No. 11/652,169, filed Jan. 11, 2007.

(Continued)

*Primary Examiner*—Scott A. Smith

(57) ABSTRACT

The present invention includes a surgical stapler having a staple cartridge, an anvil, and a cutting member having a cutting surface, wherein the cutting member is relatively movable with respect to the anvil and the staple cartridge. In at least one embodiment, the anvil is movable between an open position and a partially-closed position. When the anvil is in its partially-closed position, the anvil and the staple cartridge can be configured to capture tissue therebetween without fully compressing the tissue. In at least one embodiment, the anvil includes a proximal portion, a distal portion, and a middle portion intermediate the proximal portion and the distal portion. In these embodiments, the tissue can be captured between the proximal and distal portions of the anvil before the middle portion of the anvil is brought into contact with the tissue.

19 Claims, 36 Drawing Sheets

U.S. PATENT DOCUMENTS

| | | | |
|---|---|---|---|
| 4,728,020 A | 3/1988 | Green et al. | |
| 4,754,909 A | 7/1988 | Barker et al. | |
| 4,767,044 A | 8/1988 | Green | |
| 4,869,414 A | 9/1989 | Green et al. | |
| 4,869,415 A | 9/1989 | Fox | |
| 4,941,623 A | 7/1990 | Pruitt | |
| 4,944,443 A | 7/1990 | Oddsen et al. | |
| 5,065,929 A | 11/1991 | Schulze et al. | |
| 5,071,430 A * | 12/1991 | de Salis et al. | 606/219 |
| 5,129,570 A | 7/1992 | Schulze et al. | |
| 5,137,198 A | 8/1992 | Nobis et al. | |
| 5,221,036 A | 6/1993 | Takase | |
| 5,379,933 A | 1/1995 | Green et al. | |
| 5,389,098 A | 2/1995 | Tsuruta et al. | |
| 5,480,089 A | 1/1996 | Blewett | |
| 5,482,197 A | 1/1996 | Green et al. | |
| 5,485,947 A | 1/1996 | Olson et al. | |
| 5,485,952 A | 1/1996 | Fontayne | |
| 5,487,499 A | 1/1996 | Sorrentino et al. | |
| 5,489,058 A | 2/1996 | Plyley et al. | |
| 5,497,933 A | 3/1996 | DeFonzo et al. | |
| 5,503,320 A | 4/1996 | Webster et al. | |
| 5,503,638 A | 4/1996 | Cooper et al. | |
| 5,509,596 A | 4/1996 | Green et al. | |
| 5,529,235 A | 6/1996 | Boiarski et al. | |
| 5,535,934 A | 7/1996 | Boiarski et al. | |
| 5,540,375 A | 7/1996 | Bolanos et al. | |
| 5,549,628 A | 8/1996 | Cooper et al. | |
| 5,560,532 A | 10/1996 | DeFonzo et al. | |
| 5,562,241 A | 10/1996 | Knodel et al. | |
| 5,564,615 A | 10/1996 | Bishop et al. | |
| 5,575,803 A | 11/1996 | Cooper et al. | |
| 5,577,654 A | 11/1996 | Bishop | |
| 5,580,067 A | 12/1996 | Hamblin et al. | |
| 5,582,611 A | 12/1996 | Tsuruta et al. | |
| 5,586,711 A | 12/1996 | Plyley et al. | |
| 5,588,579 A | 12/1996 | Schnut et al. | |
| 5,588,580 A | 12/1996 | Paul et al. | |
| 5,588,581 A | 12/1996 | Conlon et al. | |
| 5,601,224 A | 2/1997 | Bishop et al. | |
| 5,603,443 A | 2/1997 | Clark et al. | |
| 5,605,273 A | 2/1997 | Hamblin et al. | |
| 5,607,094 A | 3/1997 | Clark et al. | |
| 5,628,446 A | 5/1997 | Geiste et al. | |
| 5,630,539 A | 5/1997 | Plyley et al. | |
| 5,630,540 A | 5/1997 | Blewett | |
| 5,632,432 A | 5/1997 | Schulze et al. | |
| 5,634,584 A | 6/1997 | Okorocha et al. | |
| 5,636,780 A | 6/1997 | Green et al. | |
| 5,639,008 A | 6/1997 | Gallagher et al. | |
| 5,651,491 A | 7/1997 | Heaton et al. | |
| 5,653,373 A | 8/1997 | Green et al. | |
| 5,653,374 A | 8/1997 | Young et al. | |
| 5,655,698 A | 8/1997 | Yoon | |
| 5,657,921 A | 8/1997 | Young et al. | |
| 5,662,258 A | 9/1997 | Knodel et al. | |
| 5,662,260 A | 9/1997 | Yoon | |
| 5,669,544 A | 9/1997 | Schulze et al. | |
| 5,673,840 A | 10/1997 | Schulze et al. | |
| 5,673,841 A | 10/1997 | Schulze et al. | |
| 5,680,981 A | 10/1997 | Mililli et al. | |
| 5,680,982 A | 10/1997 | Schulze et al. | |
| 5,690,269 A | 11/1997 | Bolanos et al. | |
| 5,692,668 A | 12/1997 | Schulze et al. | |
| 5,697,543 A | 12/1997 | Burdorff | |
| 5,704,534 A | 1/1998 | Huitema et al. | |
| 5,711,472 A | 1/1998 | Bryan | |
| 5,732,871 A | 3/1998 | Clark et al. | |
| 5,743,456 A | 4/1998 | Jones et al. | |
| 5,752,644 A | 5/1998 | Bolanos et al. | |
| 5,758,814 A | 6/1998 | Gallagher et al. | |
| 5,762,256 A | 6/1998 | Mastri et al. | |
| 5,779,130 A | 7/1998 | Alesi et al. | |
| 5,779,132 A * | 7/1998 | Knodel et al. | 227/176.1 |
| 5,782,397 A | 7/1998 | Koukline | |
| 5,785,232 A | 7/1998 | Vidal et al. | |
| 5,797,536 A | 8/1998 | Smith et al. | |
| 5,797,537 A | 8/1998 | Oberlin et al. | |
| 5,797,538 A | 8/1998 | Heaton et al. | |
| 5,820,009 A | 10/1998 | Melling et al. | |
| 5,826,776 A | 10/1998 | Schulze et al. | |
| 5,836,503 A | 11/1998 | Ehrenfels et al. | |
| 5,839,639 A | 11/1998 | Sauer et al. | |
| 5,855,311 A * | 1/1999 | Hamblin et al. | 227/176.1 |
| 5,865,361 A | 2/1999 | Milliman et al. | |
| 5,871,135 A | 2/1999 | Williamson, IV et al. | |
| 5,901,895 A | 5/1999 | Heaton et al. | |
| 5,911,353 A | 6/1999 | Bolanos et al. | |
| 5,941,442 A | 8/1999 | Geiste et al. | |
| 5,954,259 A | 9/1999 | Viola et al. | |
| 6,010,054 A | 1/2000 | Johnson et al. | |
| 6,032,849 A | 3/2000 | Mastri et al. | |
| 6,102,271 A | 8/2000 | Longo et al. | |
| 6,156,056 A | 12/2000 | Kearns et al. | |
| 6,202,914 B1 | 3/2001 | Geiste et al. | |
| 6,241,139 B1 | 6/2001 | Milliman et al. | |
| 6,250,532 B1 | 6/2001 | Green et al. | |
| 6,264,086 B1 | 7/2001 | McGuckin, Jr. | |
| 6,264,087 B1 | 7/2001 | Whitman | |
| 6,273,897 B1 | 8/2001 | Dalessandro et al. | |
| 6,315,184 B1 | 11/2001 | Whitman | |
| 6,325,810 B1 | 12/2001 | Hamilton et al. | |
| 6,330,965 B1 | 12/2001 | Milliman et al. | |
| 6,488,197 B1 | 12/2002 | Whitman | |
| 6,491,201 B1 | 12/2002 | Whitman | |
| 6,503,257 B2 | 1/2003 | Grant et al. | |
| 6,505,768 B2 | 1/2003 | Whitman | |
| 6,592,597 B2 | 7/2003 | Grant et al. | |
| 6,602,252 B2 | 8/2003 | Mollenauer | |
| 6,619,529 B2 | 9/2003 | Green et al. | |
| 6,620,166 B1 | 9/2003 | Wenstrom, Jr. et al. | |
| 6,644,532 B2 | 11/2003 | Green et al. | |
| 6,656,193 B2 | 12/2003 | Grant et al. | |
| 6,681,978 B2 | 1/2004 | Geiste et al. | |
| 6,681,979 B2 | 1/2004 | Whitman | |
| 6,695,199 B2 | 2/2004 | Whitman | |
| 6,698,643 B2 | 3/2004 | Whitman | |
| 6,755,338 B2 | 6/2004 | Hahnen et al. | |
| 6,786,382 B1 | 9/2004 | Hoffman | |
| 6,805,273 B2 | 10/2004 | Bilotti et al. | |
| 6,814,741 B2 | 11/2004 | Bowman et al. | |
| 6,817,508 B1 | 11/2004 | Racenet et al. | |
| 6,817,509 B2 | 11/2004 | Geiste et al. | |
| 6,821,273 B2 | 11/2004 | Mollenauer | |
| 6,830,174 B2 | 12/2004 | Hillstead et al. | |
| 6,835,199 B2 | 12/2004 | McGuckin, Jr. et al. | |
| 6,843,403 B2 | 1/2005 | Whitman | |
| RE38,708 E | 3/2005 | Bolanos et al. | |
| 6,877,647 B2 | 4/2005 | Green et al. | |
| 6,905,057 B2 | 6/2005 | Swayze et al. | |
| 6,945,444 B2 | 9/2005 | Gresham et al. | |
| 6,953,138 B1 | 10/2005 | Dworak et al. | |
| 6,953,139 B2 | 10/2005 | Milliman et al. | |
| 6,964,363 B2 | 11/2005 | Wales et al. | |
| 6,978,921 B2 | 12/2005 | Shelton, IV et al. | |
| 6,978,922 B2 | 12/2005 | Bilotti et al. | |
| 6,981,628 B2 | 1/2006 | Wales | |
| 6,986,451 B1 | 1/2006 | Mastri et al. | |
| 6,988,649 B2 * | 1/2006 | Shelton et al. | 227/175.2 |
| 6,988,650 B2 | 1/2006 | Schwemberger et al. | |
| 7,000,818 B2 | 2/2006 | Shelton, IV et al. | |
| 7,000,819 B2 | 2/2006 | Swayze et al. | |
| 7,032,798 B2 | 4/2006 | Whitman et al. | |
| 7,032,799 B2 * | 4/2006 | Viola et al. | 227/175.1 |

| | | | | | | |
|---|---|---|---|---|---|---|
| 7,044,352 | B2 | 5/2006 | Shelton, IV et al. | 2007/0175960 A1 | 8/2007 | Shelton, IV et al. |
| 7,044,353 | B2 | 5/2006 | Mastri et al. | 2007/0175961 A1 | 8/2007 | Shelton, IV et al. |
| 7,055,731 | B2 | 6/2006 | Shelton, IV et al. | 2007/0175962 A1 | 8/2007 | Shelton, IV et al. |
| 7,070,083 | B2 | 7/2006 | Jankowski | 2007/0175964 A1 | 8/2007 | Shelton, IV et al. |
| 7,083,075 | B2 | 8/2006 | Swayze et al. | 2007/0179476 A1 | 8/2007 | Shelton, IV et al. |
| 7,090,684 | B2 | 8/2006 | McGuckin, Jr. et al. | 2007/0194079 A1 | 8/2007 | Hueil et al. |
| 7,111,769 | B2 | 9/2006 | Wales et al. | 2007/0194080 A1 | 8/2007 | Swayze et al. |
| 7,114,642 | B2 | 10/2006 | Whitman | 2007/0194081 A1 | 8/2007 | Hueil et al. |
| 7,128,253 | B2 | 10/2006 | Mastri et al. | 2007/0194082 A1 | 8/2007 | Morgan et al. |
| 7,140,527 | B2 | 11/2006 | Ehrenfels et al. | 2007/0233053 A1 | 10/2007 | Shelton, IV et al. |
| 7,147,138 | B2 | 12/2006 | Shelton, IV | 2007/0262116 A1 | 11/2007 | Hueil et al. |
| 7,159,750 | B2 | 1/2007 | Racenet et al. | 2007/0295780 A1 | 12/2007 | Shelton et al. |
| 7,168,604 | B2 | 1/2007 | Milliman et al. | 2008/0029570 A1 | 2/2008 | Shelton et al. |
| 7,188,758 | B2 | 3/2007 | Viola et al. | 2008/0029571 A1 | 2/2008 | Shelton et al. |
| 7,210,609 | B2 | 5/2007 | Leiboff et al. | 2008/0029572 A1 | 2/2008 | Shelton et al. |
| 7,213,736 | B2 | 5/2007 | Wales et al. | 2008/0029573 A1 | 2/2008 | Shelton et al. |
| 7,225,964 | B2 | 6/2007 | Mastri et al. | 2008/0029574 A1 | 2/2008 | Shelton et al. |
| 7,246,734 | B2 | 7/2007 | Shelton, IV | 2008/0029575 A1 | 2/2008 | Shelton et al. |
| 7,258,262 | B2 | 8/2007 | Mastri et al. | 2008/0029576 A1 | 2/2008 | Shelton et al. |
| 7,328,828 | B2 | 2/2008 | Ortiz et al. | 2008/0029577 A1 | 2/2008 | Shelton et al. |
| 7,354,447 | B2 | 4/2008 | Shelton, IV et al. | 2008/0035701 A1 | 2/2008 | Racenet et al. |
| 2002/0117534 | A1 | 8/2002 | Green et al. | 2008/0041917 A1 | 2/2008 | Racenet et al. |
| 2004/0094597 | A1 | 5/2004 | Whitman et al. | 2008/0078800 A1 | 4/2008 | Hess et al. |
| 2004/0108357 | A1 | 6/2004 | Milliman et al. | 2008/0078801 A1 | 4/2008 | Shelton et al. |
| 2004/0164123 | A1 | 8/2004 | Racenet et al. | 2008/0078802 A1 | 4/2008 | Hess et al. |
| 2004/0173659 | A1 | 9/2004 | Green et al. | 2008/0078803 A1 | 4/2008 | Shelton et al. |
| 2004/0222268 | A1 | 11/2004 | Bilotti et al. | 2008/0078804 A1 | 4/2008 | Shelton et al. |
| 2004/0232201 | A1 | 11/2004 | Wenchell et al. | 2008/0078805 A1 | 4/2008 | Omaits et al. |
| 2004/0243151 | A1 | 12/2004 | Demmy et al. | 2008/0078806 A1 | 4/2008 | Omaits et al. |
| 2004/0243176 | A1 | 12/2004 | Hahnen et al. | 2008/0078807 A1 | 4/2008 | Hess et al. |
| 2005/0072827 | A1 | 4/2005 | Mollenauer | 2008/0078808 A1 | 4/2008 | Hess et al. |
| 2005/0103819 | A1 | 5/2005 | Racenet et al. | 2008/0082115 A1 | 4/2008 | Morgan et al. |
| 2005/0107824 | A1 | 5/2005 | Hillstead et al. | 2008/0082124 A1 | 4/2008 | Hess et al. |
| 2005/0119669 | A1 | 6/2005 | Demmy | 2008/0082125 A1 | 4/2008 | Murray et al. |
| 2005/0143759 | A1 | 6/2005 | Kelly | 2008/0082126 A1 | 4/2008 | Murray et al. |
| 2005/0145671 | A1 | 7/2005 | Viola | | | |
| 2005/0184121 | A1 | 8/2005 | Heinrich | FOREIGN PATENT DOCUMENTS | | |
| 2005/0189397 | A1 | 9/2005 | Jankowski | | | |
| 2005/0216055 | A1 | 9/2005 | Scirica et al. | CA | 2512960 A1 | 1/2006 |
| 2005/0263562 | A1 | 12/2005 | Shelton, IV et al. | CA | 2514274 A1 | 1/2006 |
| 2005/0263563 | A1 | 12/2005 | Racenet et al. | DE | 273689 C | 5/1914 |
| 2005/0274768 | A1 | 12/2005 | Cummins et al. | DE | 9412228 U | 9/1994 |
| 2006/0011699 | A1 | 1/2006 | Olson et al. | DE | 69328576 T2 | 1/2001 |
| 2006/0049229 | A1 | 3/2006 | Milliman et al. | DE | 20112837 U1 | 10/2001 |
| 2006/0151567 | A1 | 7/2006 | Roy | DE | 20121753 U1 | 4/2003 |
| 2006/0226196 | A1 | 10/2006 | Hueil et al. | DE | 10314072 A1 | 10/2004 |
| 2006/0278680 | A1 | 12/2006 | Viola et al. | EP | 0122046 A1 | 10/1984 |
| 2006/0278681 | A1 | 12/2006 | Viola et al. | EP | 0033548 B1 | 5/1986 |
| 2006/0289602 | A1 | 12/2006 | Wales et al. | EP | 0639349 A2 | 2/1994 |
| 2007/0034666 | A1 | 2/2007 | Holsten et al. | EP | 0593920 A1 | 4/1994 |
| 2007/0045379 | A1 | 3/2007 | Shelton, IV | EP | 0600182 A2 | 6/1994 |
| 2007/0073340 | A1 | 3/2007 | Shelton, IV et al. | EP | 0630612 A1 | 12/1994 |
| 2007/0075114 | A1 | 4/2007 | Shelton, IV et al. | EP | 0634144 A1 | 1/1995 |
| 2007/0083234 | A1 | 4/2007 | Shelton, IV et al. | EP | 0646356 A2 | 4/1995 |
| 2007/0084897 | A1 | 4/2007 | Shelton, IV et al. | EP | 0646357 A1 | 4/1995 |
| 2007/0102452 | A1 | 5/2007 | Shelton, IV et al. | EP | 0669104 A1 | 8/1995 |
| 2007/0102453 | A1 | 5/2007 | Morgan et al. | EP | 0679367 A2 | 11/1995 |
| 2007/0102472 | A1 | 5/2007 | Shelton, IV | EP | 0392547 B1 | 12/1995 |
| 2007/0102473 | A1 | 5/2007 | Shelton, IV et al. | EP | 0685204 A1 | 12/1995 |
| 2007/0102474 | A1 | 5/2007 | Shelton, IV et al. | EP | 0699418 A1 | 3/1996 |
| 2007/0106317 | A1 | 5/2007 | Shelton, IV et al. | EP | 0702937 A1 | 3/1996 |
| 2007/0158385 | A1 | 7/2007 | Hueil et al. | EP | 0705571 A1 | 4/1996 |
| 2007/0170225 | A1 | 7/2007 | Shelton, IV et al. | EP | 0484677 B2 | 6/1996 |
| 2007/0175949 | A1 | 8/2007 | Shelton, IV et al. | EP | 0541987 B1 | 7/1996 |
| 2007/0175950 | A1 | 8/2007 | Shelton, IV et al. | EP | 0667119 B1 | 7/1996 |
| 2007/0175951 | A1 | 8/2007 | Shelton, IV et al. | EP | 0770355 A1 | 5/1997 |
| 2007/0175952 | A1 | 8/2007 | Shelton, IV et al. | EP | 0503662 B1 | 6/1997 |
| 2007/0175953 | A1 | 8/2007 | Shelton, IV et al. | EP | 0625335 B1 | 11/1997 |
| 2007/0175955 | A1 | 8/2007 | Shelton, IV et al. | EP | 0552423 B1 | 1/1998 |
| 2007/0175956 | A1 | 8/2007 | Swayze et al. | EP | 0592244 B1 | 1/1998 |
| 2007/0175957 | A1 | 8/2007 | Shelton, IV et al. | EP | 0648476 B1 | 1/1998 |
| 2007/0175958 | A1 | 8/2007 | Shelton, IV et al. | EP | 0603472 B1 | 11/1998 |
| 2007/0175959 | A1 | 8/2007 | Shelton, IV et al. | EP | 0878169 A1 | 11/1998 |

| | | | |
|---|---|---|---|
| EP | 0760230 B1 | 2/1999 |
| EP | 0537572 B1 | 6/1999 |
| EP | 0552050 B1 | 5/2000 |
| EP | 1090592 A1 | 4/2001 |
| EP | 1256318 B1 | 5/2001 |
| EP | 0908152 B1 | 1/2002 |
| EP | 0872213 B1 | 5/2002 |
| EP | 1238634 A2 | 9/2002 |
| EP | 0656188 B1 | 1/2003 |
| EP | 0829235 B1 | 6/2003 |
| EP | 0813843 B1 | 10/2003 |
| EP | 0705570 B1 | 4/2004 |
| EP | 1086713 B1 | 5/2004 |
| EP | 1426012 A1 | 6/2004 |
| EP | 0888749 B1 | 9/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 1520523 A1 | 4/2005 |
| EP | 1520525 A1 | 4/2005 |
| EP | 1522264 A1 | 4/2005 |
| EP | 1550408 A1 | 7/2005 |
| EP | 1557129 A1 | 7/2005 |
| EP | 1064883 B1 | 8/2005 |
| EP | 1621141 A2 | 2/2006 |
| EP | 1652481 A2 | 5/2006 |
| EP | 1382303 B1 | 6/2006 |
| EP | 1045672 B1 | 8/2006 |
| EP | 1617768 B1 | 8/2006 |
| EP | 1702567 A2 | 9/2006 |
| EP | 1129665 B1 | 11/2006 |
| EP | 1256317 B1 | 12/2006 |
| EP | 1728473 A1 | 12/2006 |
| EP | 1728475 A2 | 12/2006 |
| EP | 1479346 B1 | 1/2007 |
| EP | 1484024 B1 | 1/2007 |
| EP | 1300117 B1 | 8/2007 |
| FR | 1112936 A | 3/1956 |
| GB | 939929 A | 10/1963 |
| GB | 2336214 A | 10/1999 |
| JP | 6007357 A | 1/1994 |
| JP | 7051273 A | 2/1995 |
| JP | 8033641 A | 2/1996 |
| JP | 8229050 A | 9/1996 |
| JP | 2001286477 A | 10/2001 |
| JP | 2002/369820 A | 12/2002 |
| JP | 2005505322 T | 2/2005 |
| JP | 2005/103293 A | 4/2005 |
| RU | 2187249 C2 | 8/2002 |
| RU | 2225170 C2 | 3/2004 |
| SU | 1377053 A1 | 2/1988 |
| SU | 1561964 A1 | 5/1990 |
| SU | 1722476 A1 | 3/1992 |
| WO | WO 93/08755 A1 | 5/1993 |
| WO | WO 95/18572 A1 | 7/1995 |
| WO | WO 95/29639 A1 | 11/1995 |
| WO | WO 96/35464 A1 | 11/1996 |
| WO | WO 98/30153 A1 | 7/1998 |
| WO | WO 99/12483 A1 | 3/1999 |
| WO | WO 99/15086 A1 | 4/1999 |
| WO | WO 99/34744 A1 | 7/1999 |
| WO | WO 00/57796 A1 | 10/2000 |
| WO | WO 00/72762 A1 | 12/2000 |
| WO | WO 00/72765 A1 | 12/2000 |
| WO | WO 01/05702 A1 | 1/2001 |
| WO | WO 01/10482 A1 | 2/2001 |
| WO | WO 01/62158 A2 | 8/2001 |
| WO | WO 01/62162 A1 | 8/2001 |
| WO | WO 01/62164 A2 | 8/2001 |
| WO | WO 01/91646 A1 | 12/2001 |
| WO | WO 02/17799 A1 | 3/2002 |
| WO | WO 02/30297 A2 | 4/2002 |
| WO | WO 02/32322 A2 | 4/2002 |
| WO | WO 02/43571 A2 | 6/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/020106 A2 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105702 A2 | 12/2003 |
| WO | WO 2004/006980 A2 | 1/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/047653 A2 | 6/2004 |
| WO | WO 2004/049956 A2 | 6/2004 |
| WO | WO 2004/086987 A1 | 10/2004 |
| WO | WO 2004/096057 A2 | 11/2004 |
| WO | WO 2004/112618 A2 | 12/2004 |
| WO | WO 2005/027983 A2 | 3/2005 |
| WO | WO 2005/096954 A2 | 10/2005 |
| WO | WO 2005/115251 A2 | 12/2005 |
| WO | WO 2006/044490 A2 | 4/2006 |
| WO | WO 2006/044581 A2 | 4/2006 |
| WO | WO 2006/044810 A2 | 4/2006 |
| WO | WO 2006/083748 A1 | 8/2006 |
| WO | WO 2006/132992 A1 | 12/2006 |
| WO | WO 2007/016290 A2 | 2/2007 |

OTHER PUBLICATIONS

U.S. Appl. No. 11/652,166, filed Jan. 11, 2007.
U.S. Appl. No. 11/652,165, filed Jan. 11, 2007.
U.S. Appl. No. 11/652,164, filed Jan. 11, 2007.
U.S. Appl. No. 11/652,423, filed Jan. 11, 2007.
U.S. Appl. No. 11/652,170, filed Jan. 11, 2007.
Disclosed Anonymously, "Motor-Driven Surgical Stapler Improvements," Research Disclosure Database No. 526041, Published: Feb. 2008.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

* cited by examiner

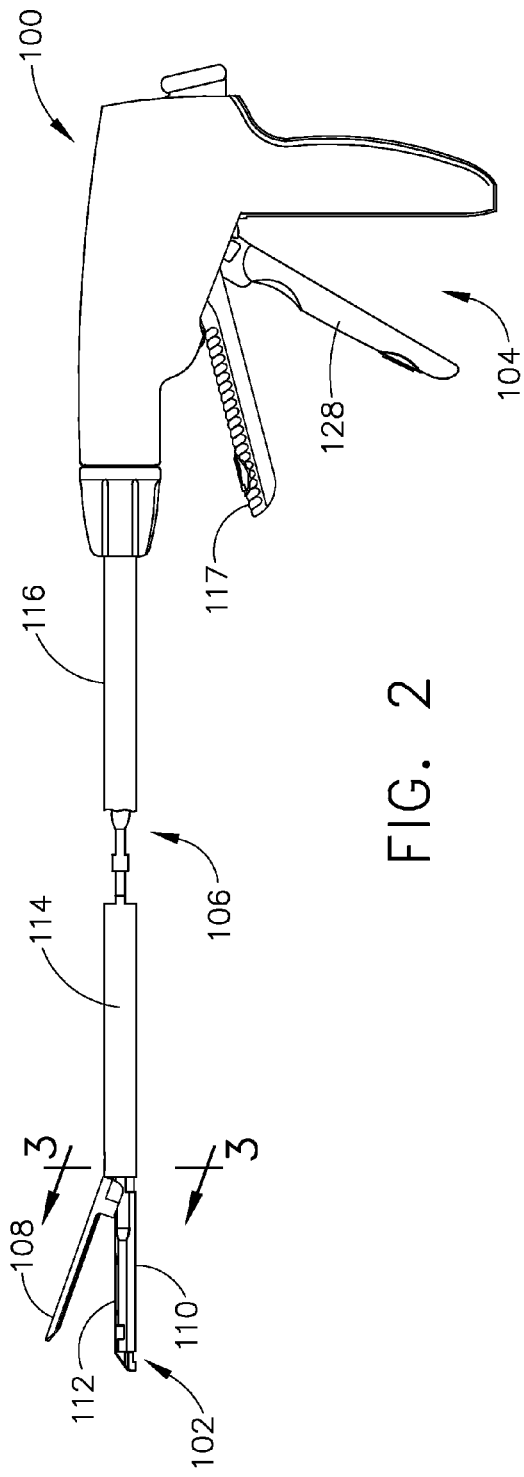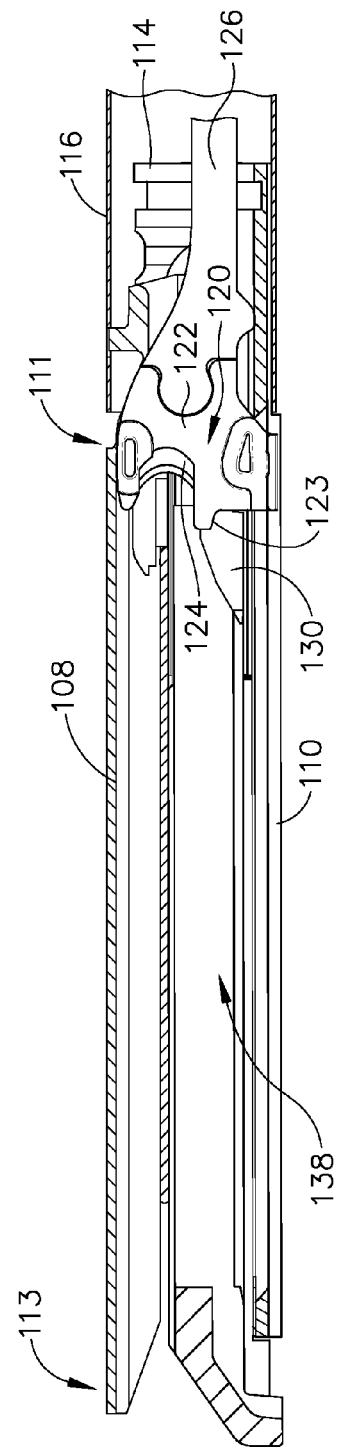

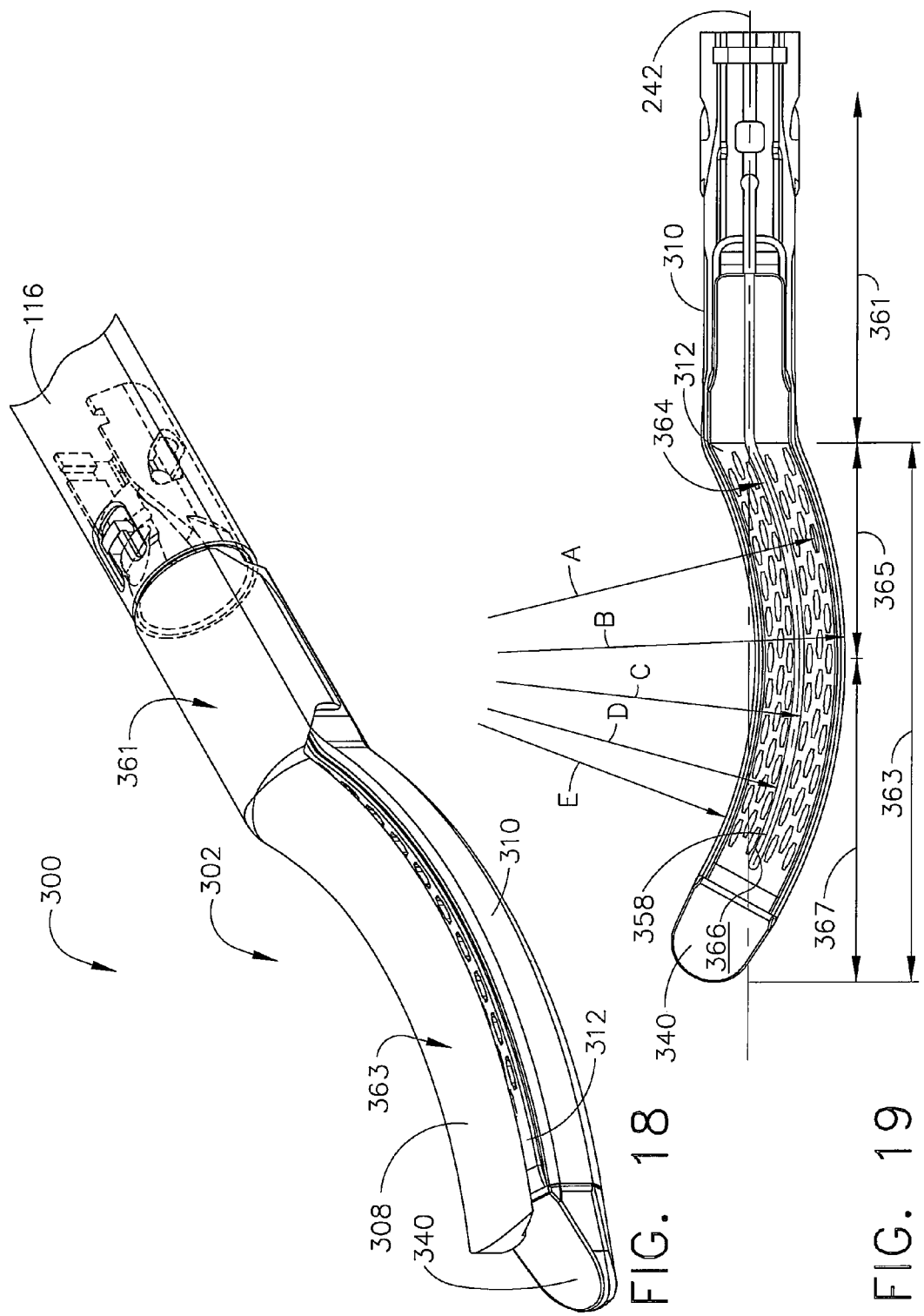

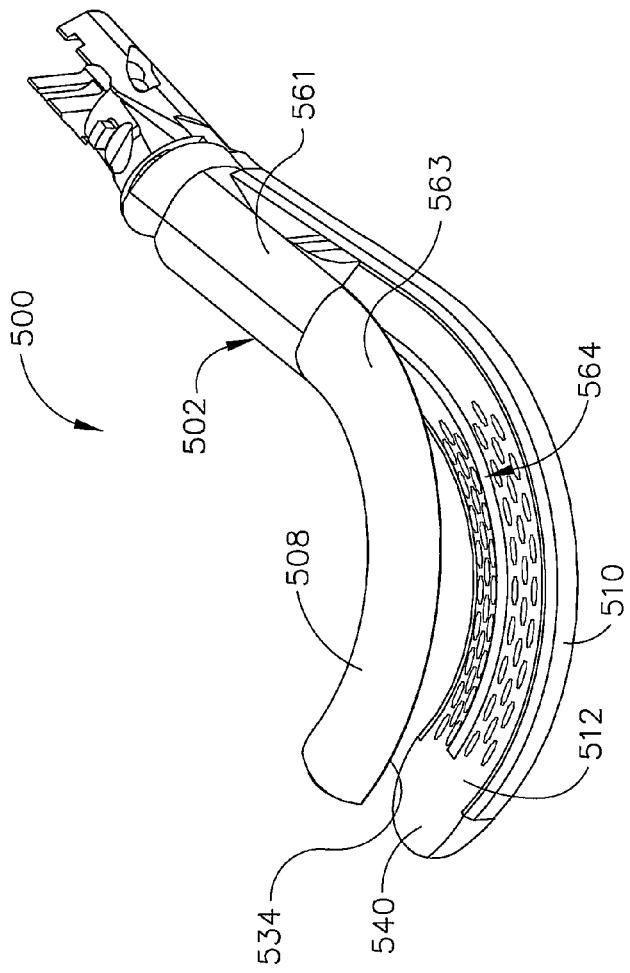
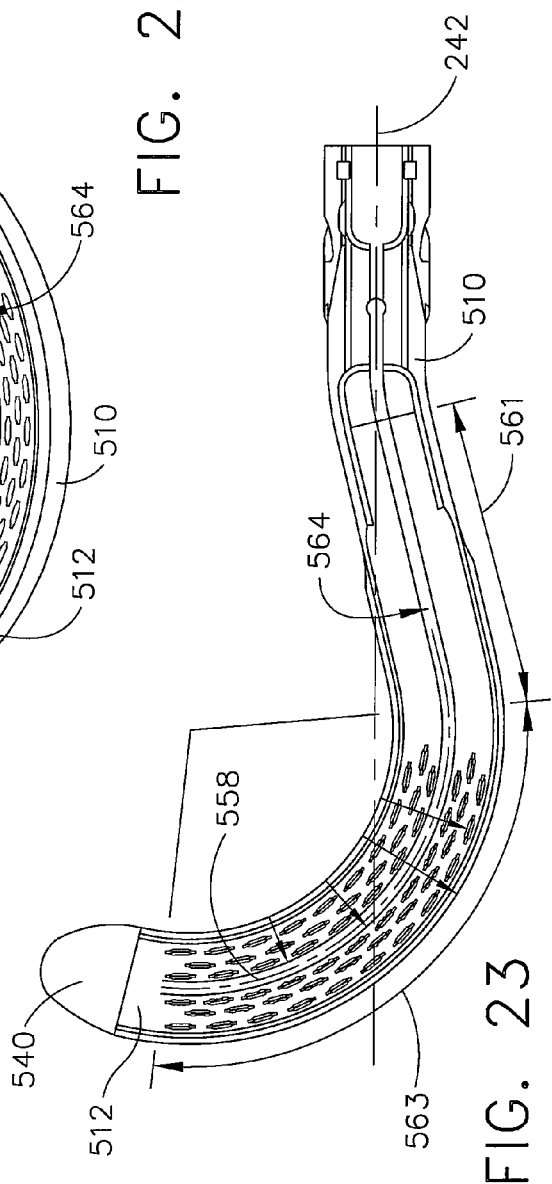
FIG. 22
FIG. 23

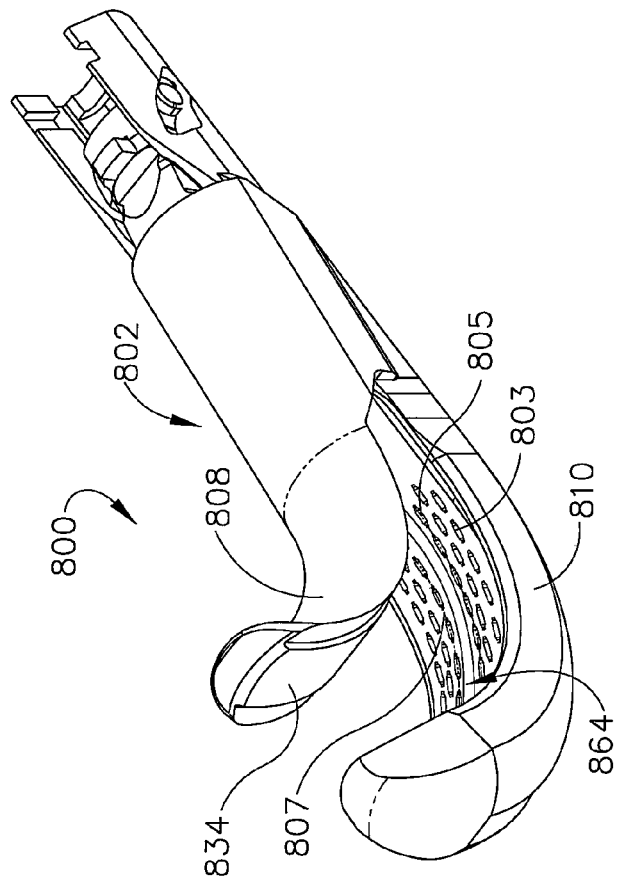
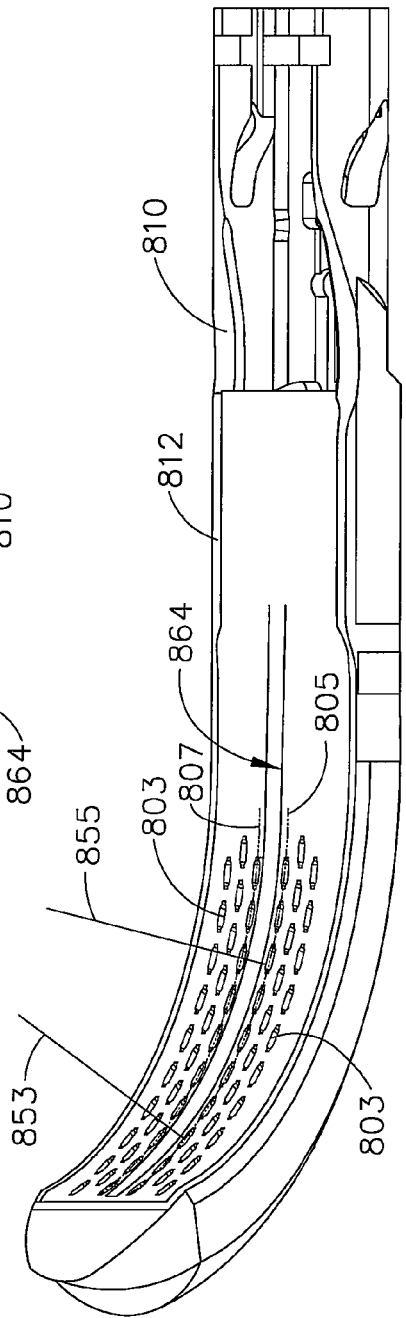
FIG. 38
FIG. 39

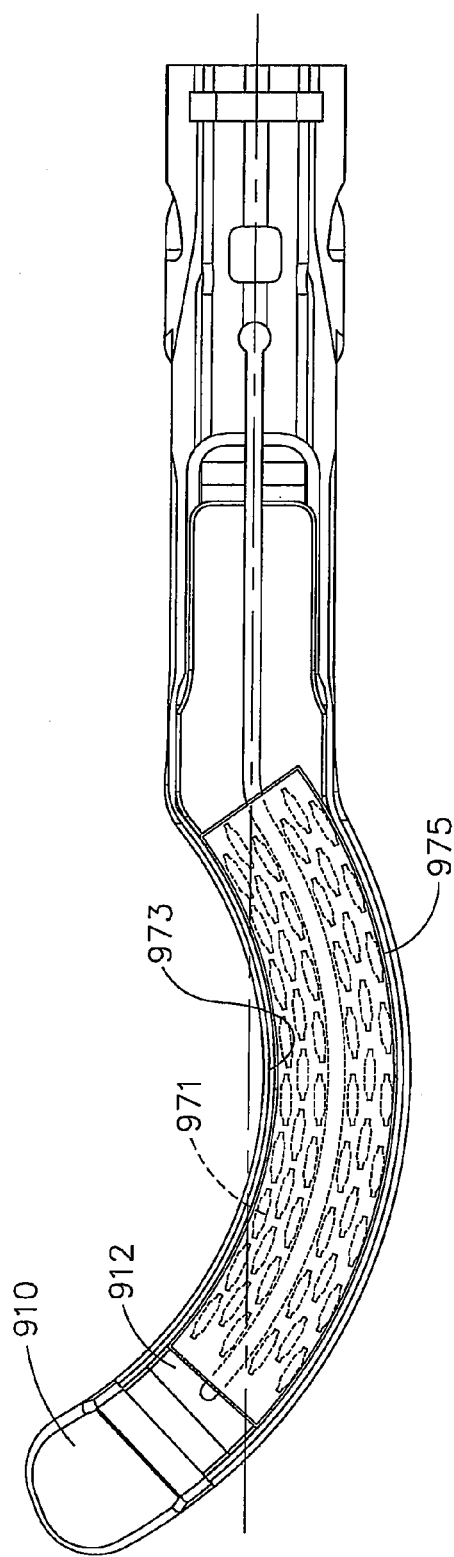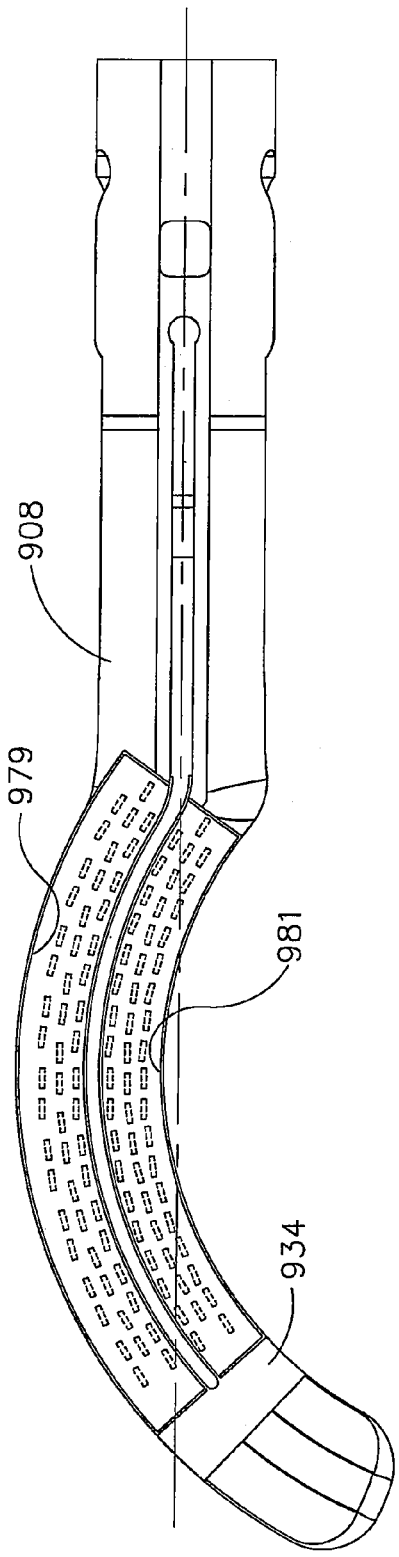
FIG. 45
FIG. 46

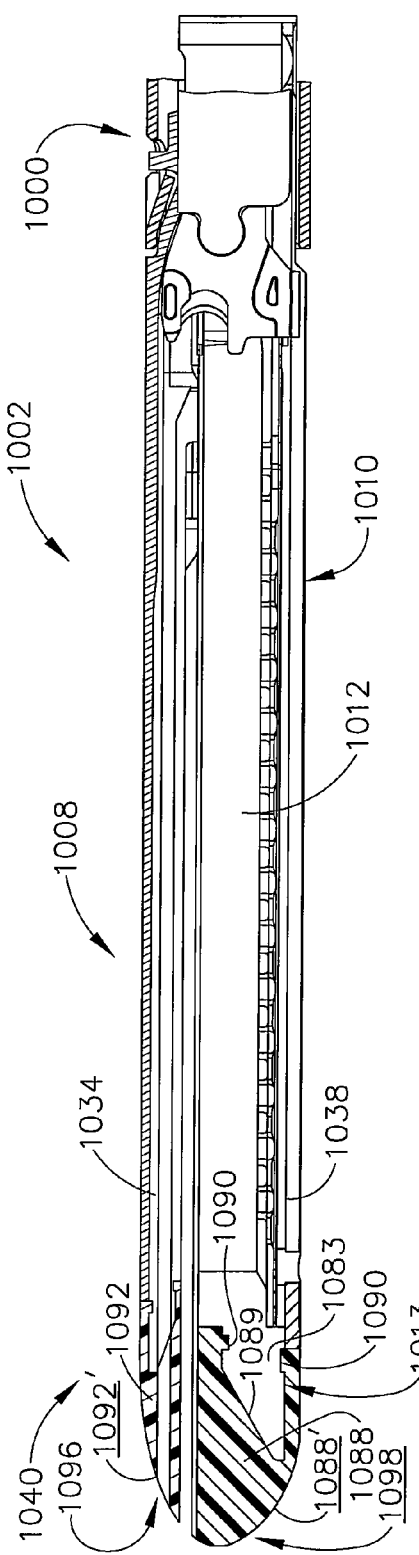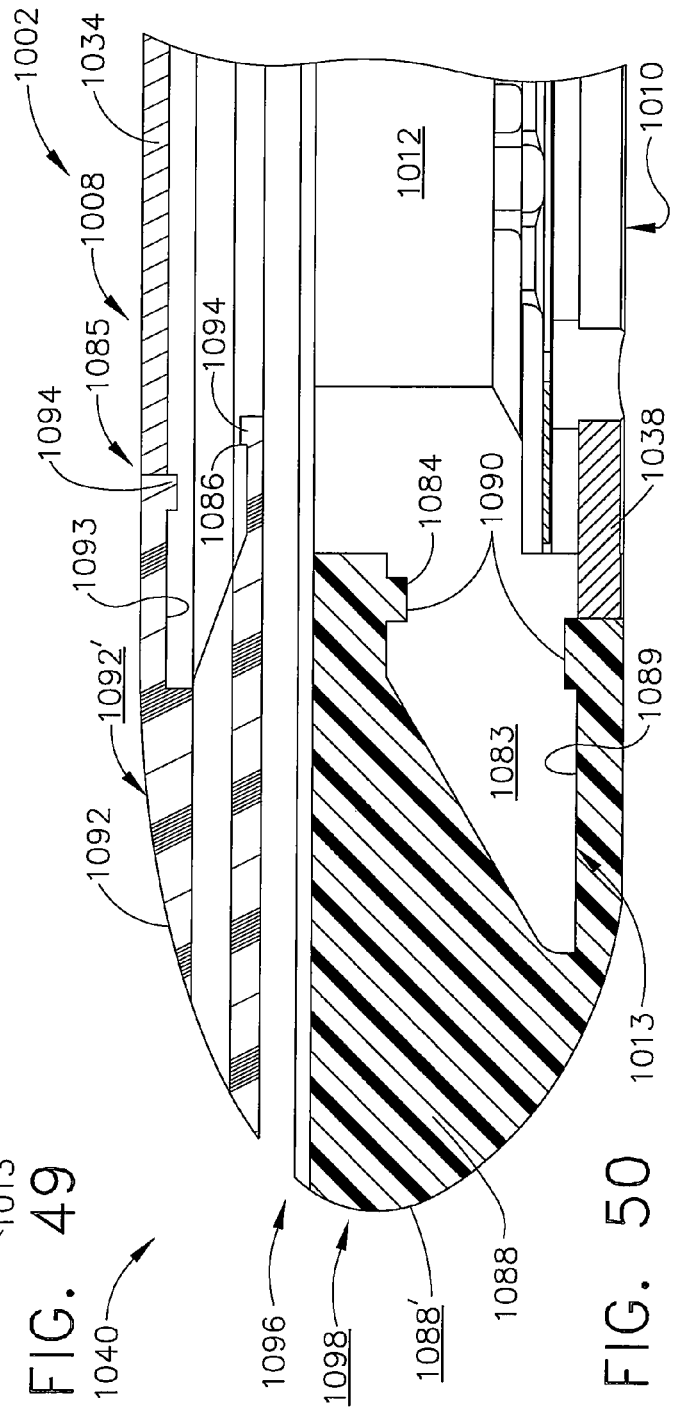
FIG. 49
FIG. 50

APPARATUS FOR CLOSING A CURVED ANVIL OF A SURGICAL STAPLING DEVICE

CROSS REFERENCE TO RELATED APPLICATIONS

The subject application is related to six co-pending and commonly-owned applications filed on even date herewith, the disclosure of each is hereby incorporated by reference in their entirety, these six applications being respectively entitled:

(1) Surgical Stapling Device With a Curved Cutting Member to Frederick E. Shelton, IV, and Jerome R. Morgan, U.S. patent application Ser. No. 11/652,169;

(2) Surgical Stapling Device Having Supports for a Flexible Drive Mechanism to Frederick E. Shelton, IV, and Jerome R. Morgan, U.S. patent application Ser. No. 11/652,166;

(3) Surgical Stapling Device With a Curved End Effector to Frederick E. Shelton, IV, Jerome R. Morgan, and Stephen J. Balek, U.S. patent application Ser. No. 11/652,165;

(4) Improved Curved End Effector for a Surgical Stapling Device to Frederick E. Shelton, IV, Jerome R. Morgan, Stephen J. Balek, and Douglas Siebenaler, U.S. patent application Ser. No. 11/652,164;

(5) Improved Buttress Material For Use With a Surgical Stapler to Frederick E. Shelton, IV, U.S. patent application Ser. No. 11/652,423; and (6) Surgical Stapler End Effector With Tapered Distal End to Frederick E. Shelton, IV, and Jerome R. Morgan, U.S. patent application Ser. No. 11/652,170.

BACKGROUND

1. Field of the Invention

The present invention generally relates to surgical staplers, and, more particularly, to surgical staplers having a curved end-effector and to surgical techniques for using the same.

2. Description of the Related Art

As known in the art, surgical staplers are often used to deploy staples into soft tissue to reduce or eliminate bleeding from the soft tissue, especially as the tissue is being transected, for example. Surgical staplers, such as an endocutter, for example, often comprise an end-effector which is configured to secure the soft tissue between first and second jaw members. The first jaw member often includes a staple cartridge which is configured to removably store staples therein and the second jaw member often includes an anvil. In use, the staples are typically deployed from the staple cartridge by a driver which traverses a channel in the staple cartridge. The driver causes the staples to be deformed against the anvil and secure layers of the soft tissue together. Often, as known in the art, the staples are deployed in several staple lines, or rows, in order to more reliably secure the layers of tissue together. The end-effector may also include a cutting member, such as a knife, for example, which is advanced between two rows of the staples to resect the soft tissue after the layers of the soft tissue have been stapled together.

The end-effectors of previous endocutters are often configured to deploy staples in straight lines. During many surgical techniques, such as the resection of stomach tissue, for example, such a linear deployment is often preferred. During these techniques, the end-effector is typically inserted through a cannula to access the surgical site and, as a result, it is often desirable for the end-effector to have a linear configuration that can be aligned with an axis of the cannula before the end-effector is inserted therethrough. However, in some circumstances, end-effectors having such a linear configuration are somewhat difficult to use. More particularly, for example, when the end-effector must be placed adjacent to or against a cavity wall, such as the thoracic cavity wall, for example, it is often difficult for the surgeon to position a jaw of the end effector behind delicate or fragile tissue which is proximal to and/or attached to the cavity wall. Furthermore, even if the surgeon is successful in positioning a jaw behind the tissue, owing to the linear configuration of the end-effector, the surgeon may not be able to see the distal end of the end-effector.

In some circumstances, endocutters having a curved end-effector have been used for accessing, stapling and transecting tissue. These end-effectors typically include curved anvils and staple cartridges which co-operate to deploy the staples in curved rows. To deploy the staples in this manner, the staple driver and the cutting member can be moved through a curved path by a flexible drive member. However, owing to the amount of force that is typically transmitted through the flexible drive member, the drive member may buckle or otherwise deform in an unsuitable manner. Furthermore, previous curved end-effectors are configured such that the distal ends of the jaw members are the last portions of the jaw members to contact the soft tissue. As a result, tissue may escape from between the jaw members before the jaw members are completely closed. What is needed is an improvement over the foregoing.

SUMMARY

In various embodiments, the present invention includes a surgical stapler having a staple cartridge configured to removably store staples therein, an anvil configured to deform the staples, and a cutting member having a cutting surface, wherein the cutting member is relatively movable with respect to the anvil and the staple cartridge. In at least one embodiment, the anvil is movable between an open position and a partially-closed position. When the anvil is in its partially-closed position, the anvil and the staple cartridge can be configured to capture tissue therebetween without fully compressing the tissue. In at least one embodiment, the anvil includes a proximal portion, a distal portion, and a middle portion intermediate the proximal portion and the distal portion. In these embodiments, the tissue can be captured between the proximal and distal portions of the anvil before the middle portion of the anvil is brought into contact with the tissue. In at least one embodiment, the anvil can include first and second edges extending between its proximal portion and its distal portion. In these embodiments, the first edge can be positioned closer to the staple cartridge than the second edge when the anvil is in its partially-closed position. In various embodiments, the anvil and staple cartridge are curved and are configured to deploy staples in at least one curved staple line.

BRIEF DESCRIPTION OF THE FIGURES

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 2 is a partial cut-away view of the endocutter of FIG. 1;

FIG. 3 is a partial cross-sectional view of the endocutter of FIG. 2 taken along line 3-3 in FIG. 2;

FIG. 18 is a perspective view of an endocutter having a curved end-effector in accordance with an alternative embodiment of the present invention;

FIG. 19 is a top view of the staple cartridge of the end-effector of FIG. 18;

FIG. 22 is a perspective view of an endocutter having a curved end-effector in accordance with an alternative embodiment of the present invention;

FIG. 23 is a top view of the staple cartridge of the end-effector of FIG. 22;

FIG. 38 is a perspective view of an endocutter having a curved end-effector in accordance with an alternative embodiment of the present invention;

FIG. 39 is a perspective view of the staple cartridge of the end-effector of FIG. 38;

FIG. 45 is a top view of the staple cartridge of FIG. 44 illustrating a piece of buttress material positioned thereon;

FIG. 46 is a bottom view of the anvil of FIG. 44 illustrating two pieces of buttress material positioned thereon;

FIG. 49 is a cross-sectional view of the end effector of FIG. 48 taken along line 49-49 in FIG. 48; and FIG. 50 is an enlarged cross-sectional view of the distal end of the end effector of FIG. 49.

Figure 1:
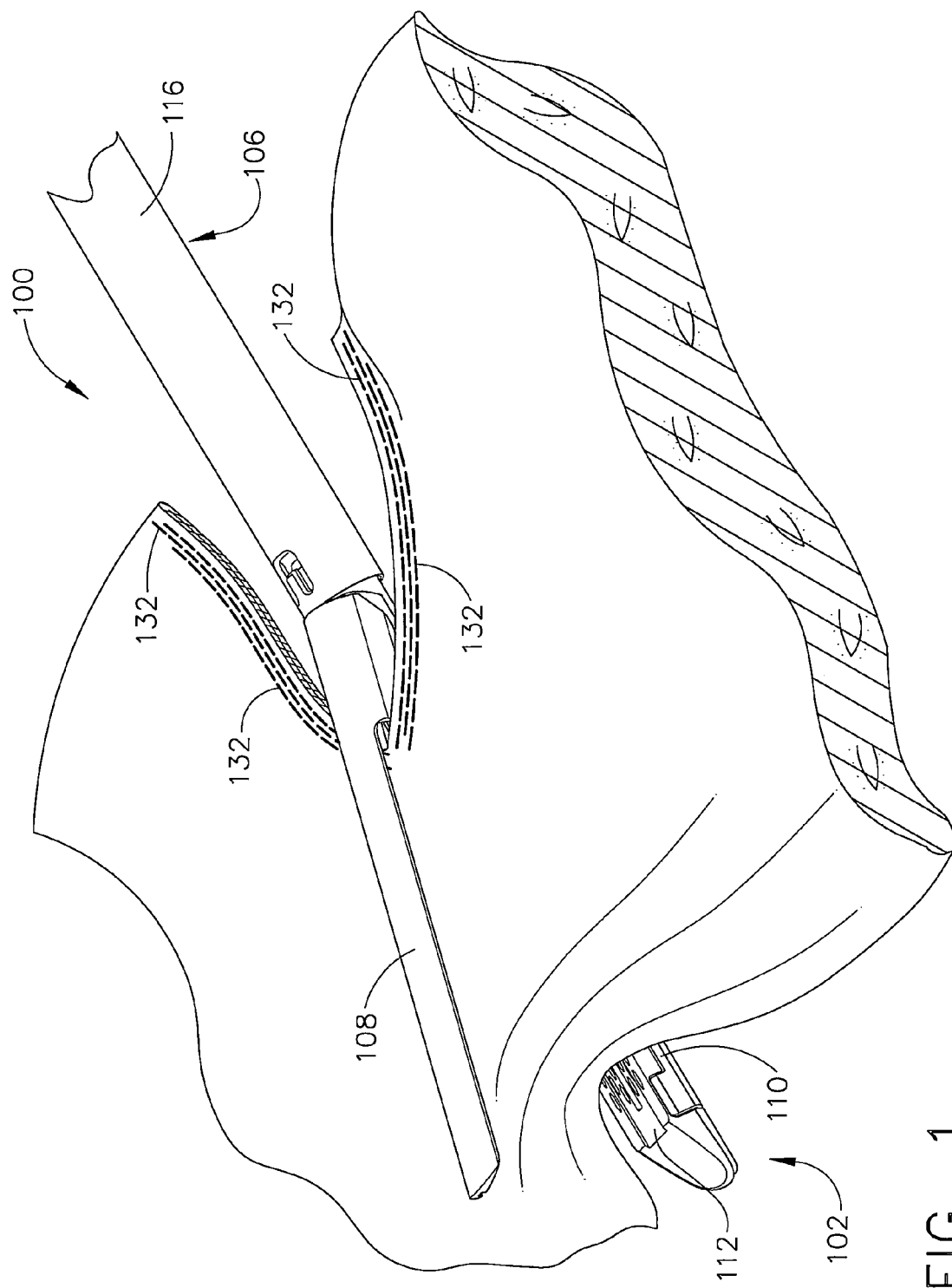
FIG. 1 is a schematic of an endocutter being used to transect and staple tissue.
Figure 4:
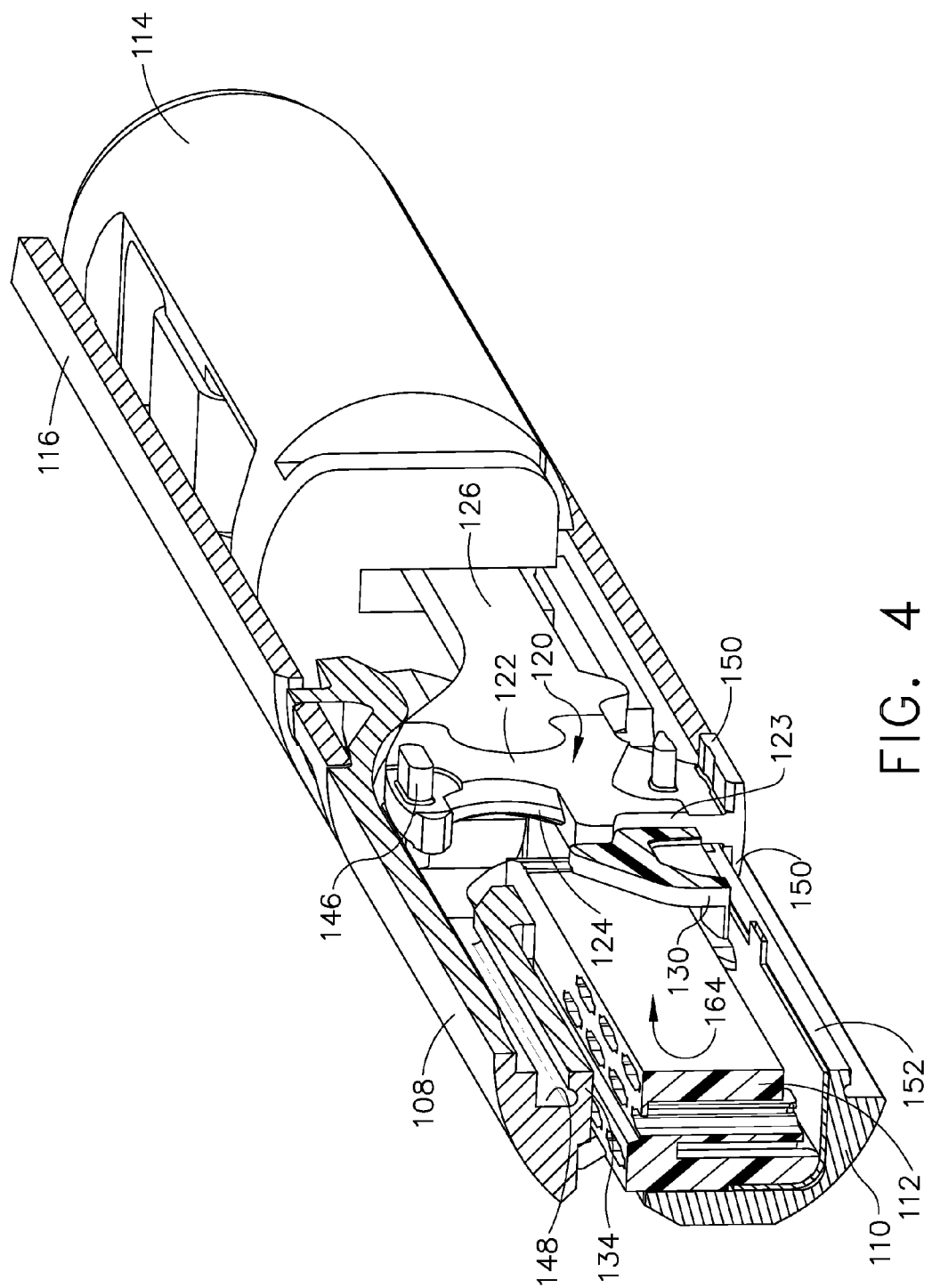
FIG. 4 is a perspective cut-away view of the endocutter of FIG. 2.

Corresponding reference characters indicate corresponding parts throughout the several views. The exemplifications set out herein illustrate preferred embodiments of the invention, in various forms, and such exemplifications are not to be construed as limiting the scope of the invention in any manner.

DETAILED DESCRIPTION

As known in the art, it is often necessary to resect tissue from a patient after the tissue has become necrotic or cancerous, for example. Frequently, blood vessels within the tissue are transected as the tissue is being cut. As a result, blood may flow from the blood vessels and complicate the surgery or endanger the patient. Often, a surgical stapler is used to secure and compress several layers of tissue together in order to substantially close the blood vessels. For example, referring to FIG. 1, a surgical stapler, such as an endocutter, can include devices which staple and then cut the tissue. As a result, the blood vessels can be substantially closed by the staples before the tissue is cut, thereby reducing bleeding therefrom.

Referring to FIGS. 1 and 2, endocutters, such as endocutter 100, for example, typically include an end-effector 102, a handle portion 104 (FIG. 2), and a shaft 106 extending therebetween. End-effector 102 includes first jaw 108 and second jaw 110 which can be configured in one of an open or a closed configuration. In their open configuration, jaws 108 and 110 can be configured to receive soft tissue therebetween, for example, allowing jaws 108 and 110 to be placed on opposite sides thereof. To close the jaws and secure the tissue therebetween, at least one of the jaws is moved against the tissue such that it holds the tissue against the opposing jaw. In the illustrated embodiment, jaw 108 is moved relative to jaw 110. Once closed, as known in the art, an anti-firing mechanism can be released allowing cutting member 120 to be advanced toward the tissue. Thereafter, as described in greater detail below, staples 132 can be deployed from staple cartridge 112 in jaw 110 to secure the layers of tissue together. Such mechanisms are described in greater detail in U.S. Pat. No. 7,000,818, the disclosure of which is hereby incorporated by reference herein.

Figure 5:
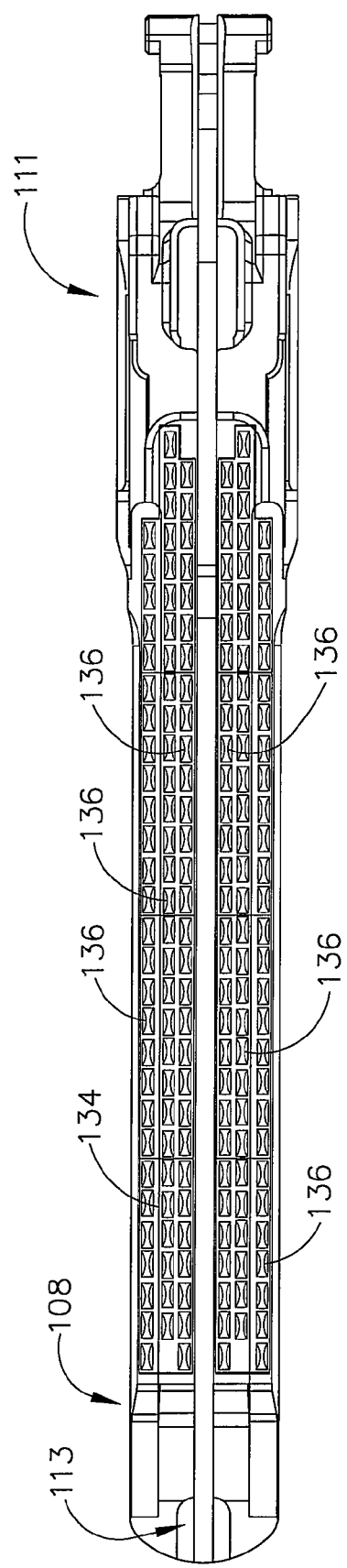
FIG. 5 is a bottom view of the anvil of the endocutter of FIG. 2.
Figure 6:
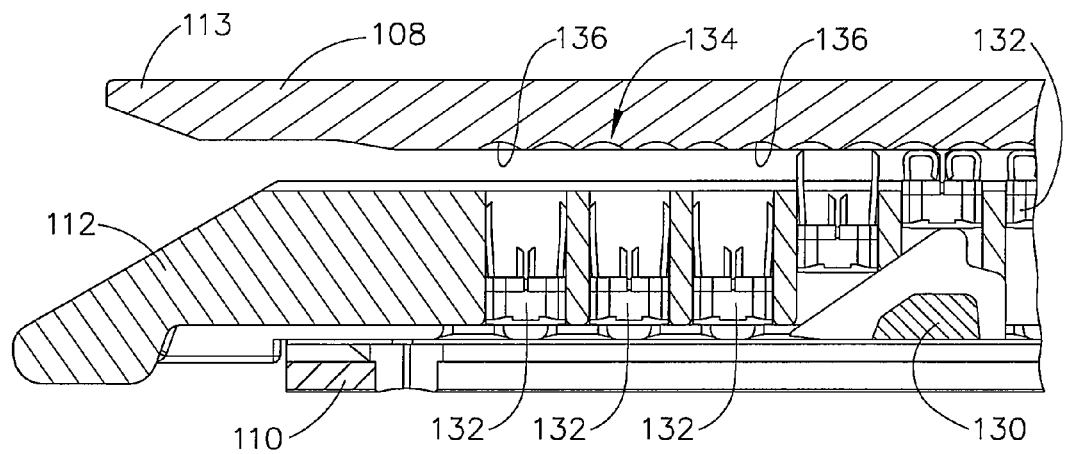
FIG. 6 is a schematic view of staples being deployed from the staple cartridge of the endocutter of FIG. 2 by a staple driver.
Figure 7:
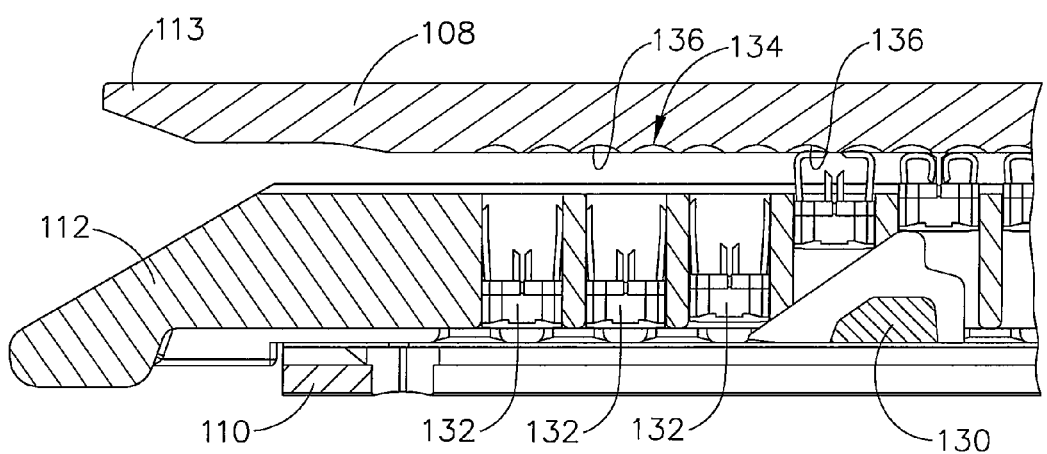
FIG. 7 is a schematic view of staples being deployed from the staple cartridge of FIG. 2 where the staple driver has been advanced within the staple cartridge with respect to its position in FIG. 6.
Figure 8:
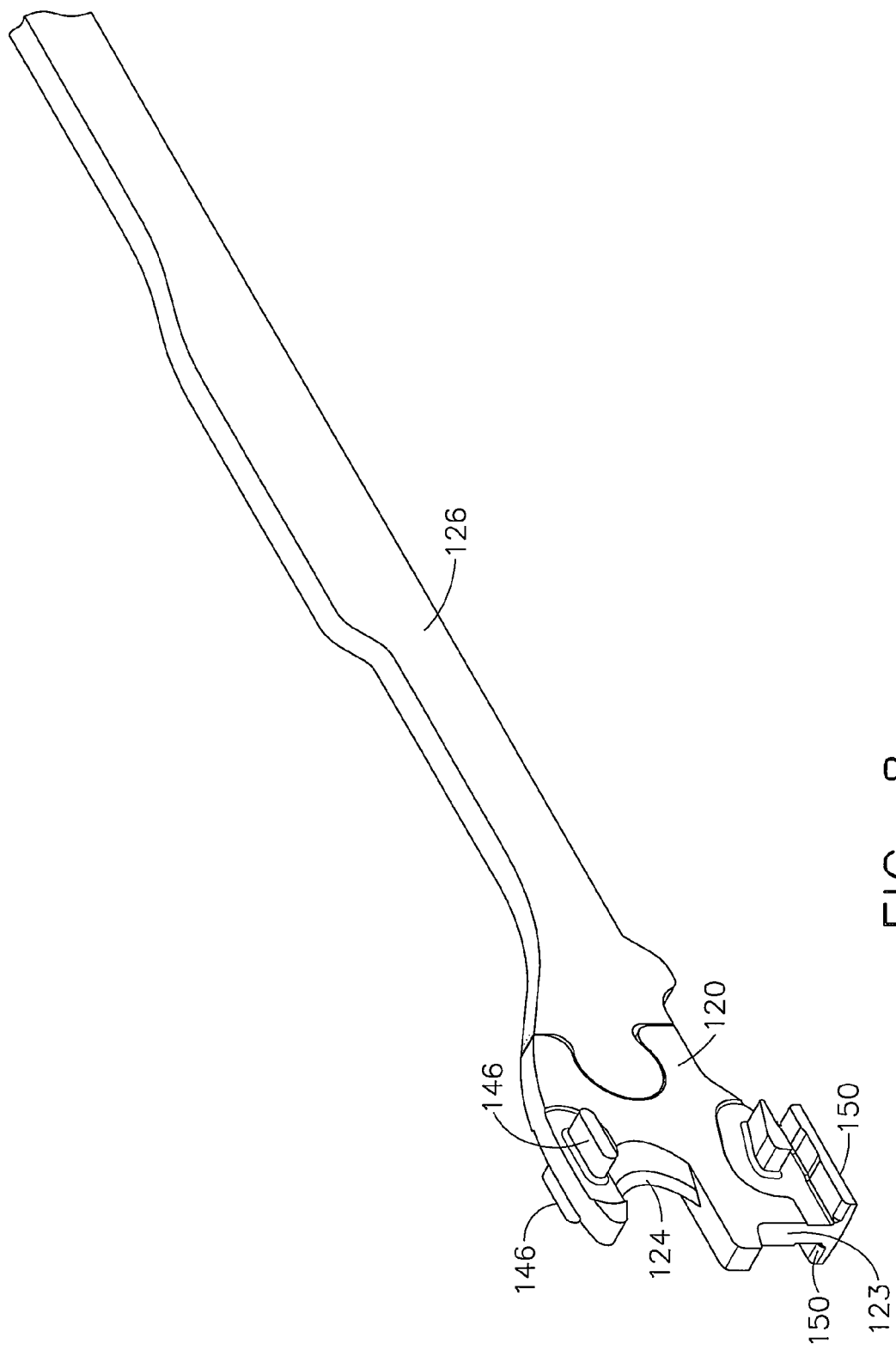
FIG. 8 is a perspective view of the cutting member and drive bar of the endocutter of FIG. 2.

Referring to FIGS. 3-4 and 6-8, cutting member 120 includes body 122 and cutting surface 124. Cutting member 120 is operably engaged with firing trigger 128 of handle portion 104 via drive bar 126 wherein the actuation of firing trigger 128 advances drive bar 126 and cutting member 120 toward the distal ends of jaws 108 and 110. In various embodiments, firing trigger 128 can activate a firing drive system which may be manually, electrically, or pneumatically driven. Cutting member body 122 further includes distal portion 123 which is configured to engage a staple driver 130 commonly supported within staple cartridge 112 and advance staple driver 130 therein. As staple driver 130 is advanced, staples 132 are lifted by driver 130 toward anvil 134. Referring to FIG. 5, anvil 134 includes pockets 136 which are configured to deform the legs of staples 132 and capture the layers of tissue therein in a known manner. In the present embodiment, as staple driver 130 is advanced, cutting member 120 is also advanced to resect the tissue after it has been stapled. In other embodiments, cutting member 120 can be configured to resect the tissue during or before the tissue has been stapled.

Figure 9:
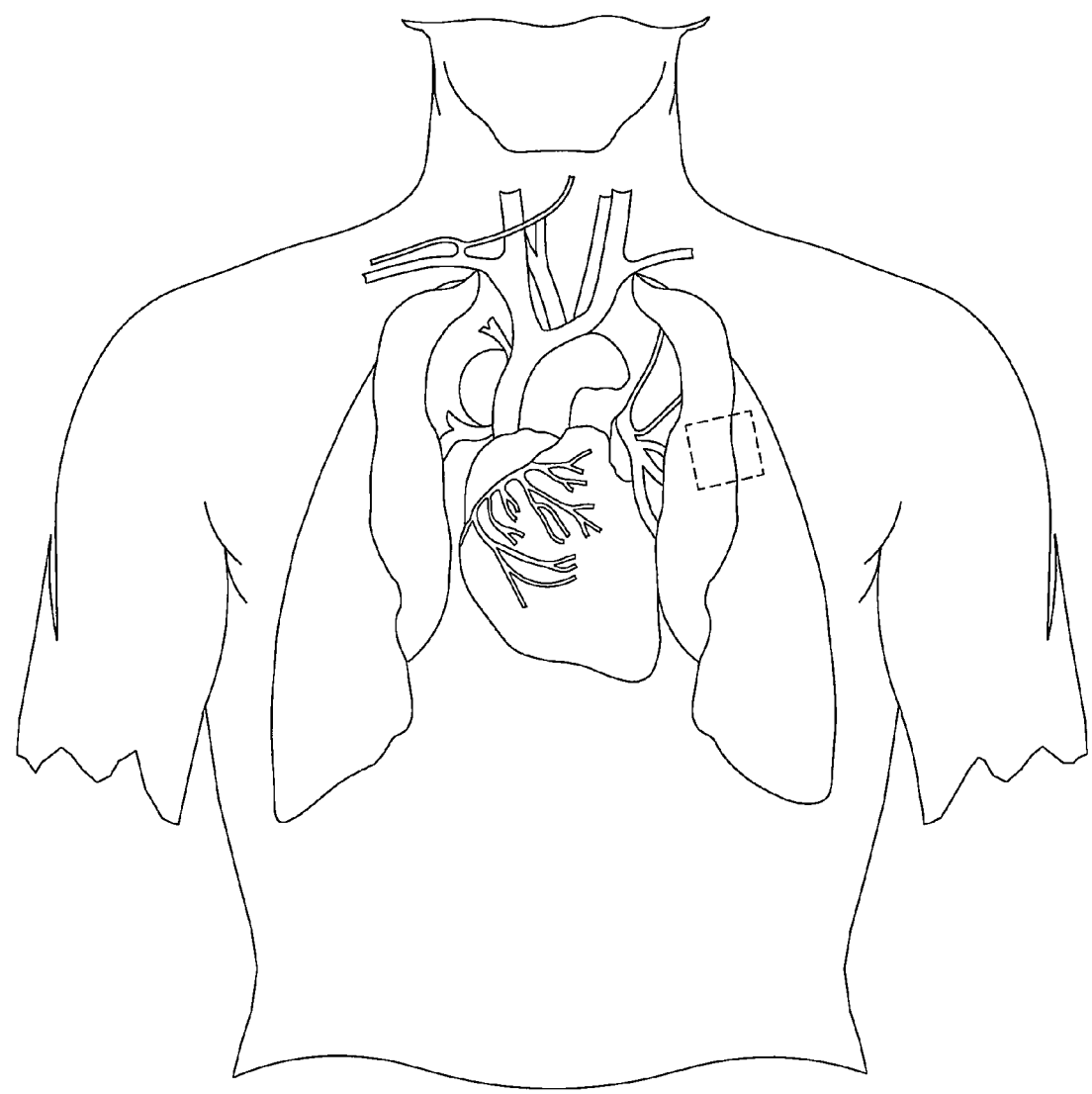
FIG. 9 is a schematic of an opened thoracic cavity.

Referring to FIGS. 1-7, the end-effector of many typical endocutters is linear, i.e., it is configured to deploy staples in straight lines. In these endocutters, drive bar 126 is configured to move cutting member 120 in a straight line and, accordingly, drive bar 126 is rigid such that it does not substantially deflect when the force to deploy the staples and transect the tissue is transmitted therethrough. In addition to the above, a variety of other drive arrangements are known for deploying staples in straight lines while resecting the tissue located between opposite lines of staples. However, it is often difficult to position such linear end-effectors in a surgical site. During at least one surgical technique, referring to FIGS. 9 and 10, an endocutter is used to transect and staple a pulmonary artery (PA) during a partial or total pneumonectomy. During this technique, the end-effector is typically placed against the wall of the thoracic cavity (TCW) such that jaw 110, and staple cartridge 112, are positioned behind the pulmonary artery. However, as the wall of the thoracic cavity is typically curved, it is often difficult to position linear jaw 110 behind the pulmonary artery. Furthermore, even if the surgeon is successful in positioning a jaw behind the pulmonary artery, the surgeon, owing to the linear configuration of the end-effector, cannot readily see the end of the jaw as it is typically hidden behind the pulmonary artery. As a result, it is difficult for the surgeon to readily determine whether the end of the jaw extends beyond the pulmonary artery, i.e., whether the pulmonary artery is entirely captured between the jaws of the end-effector.

Figure 10:
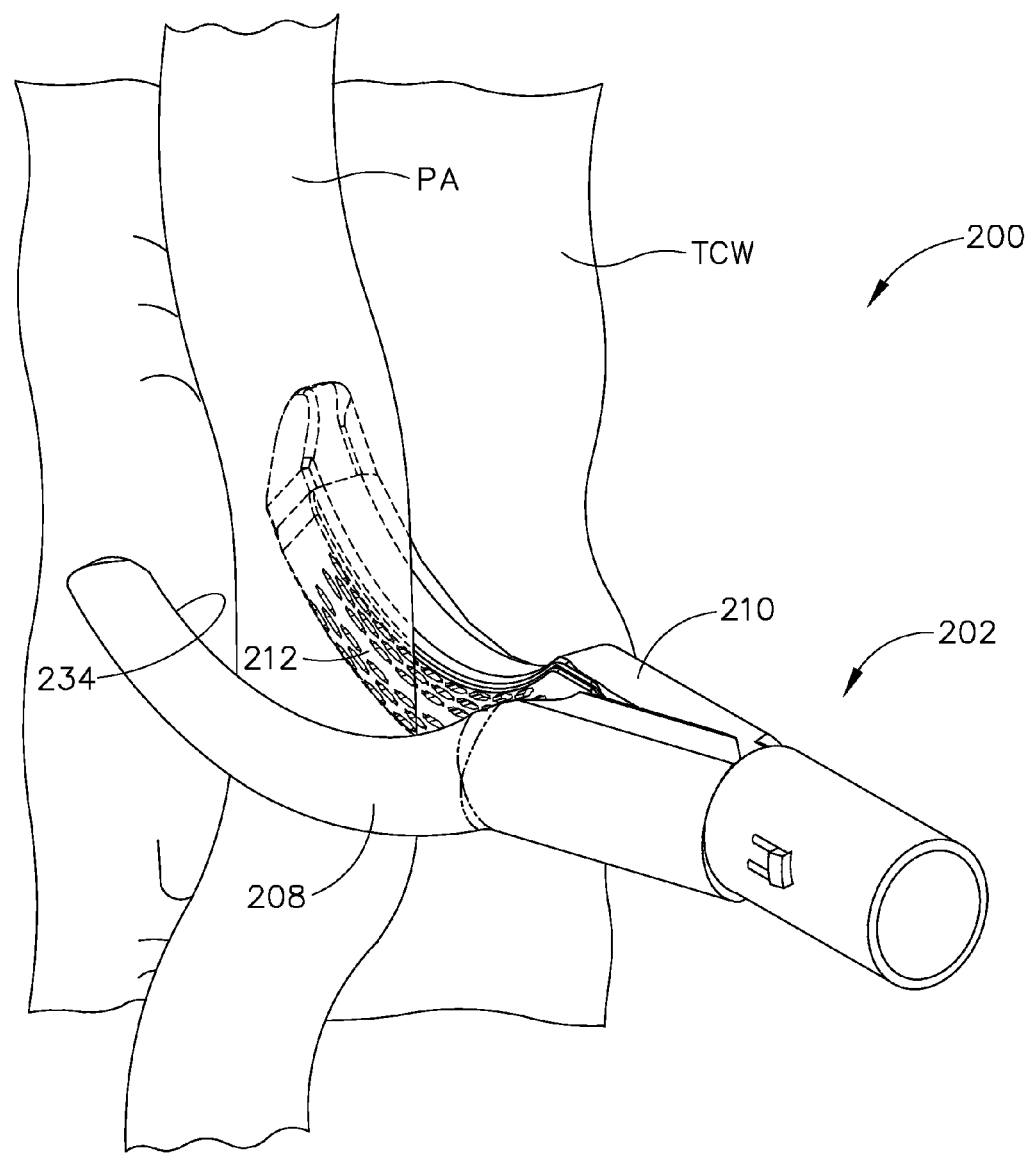
FIG. 10 is a schematic of an endocutter having a curved end-effector in accordance with an embodiment of the present invention being positioned against the side wall of a thoracic cavity.
Figure 11:
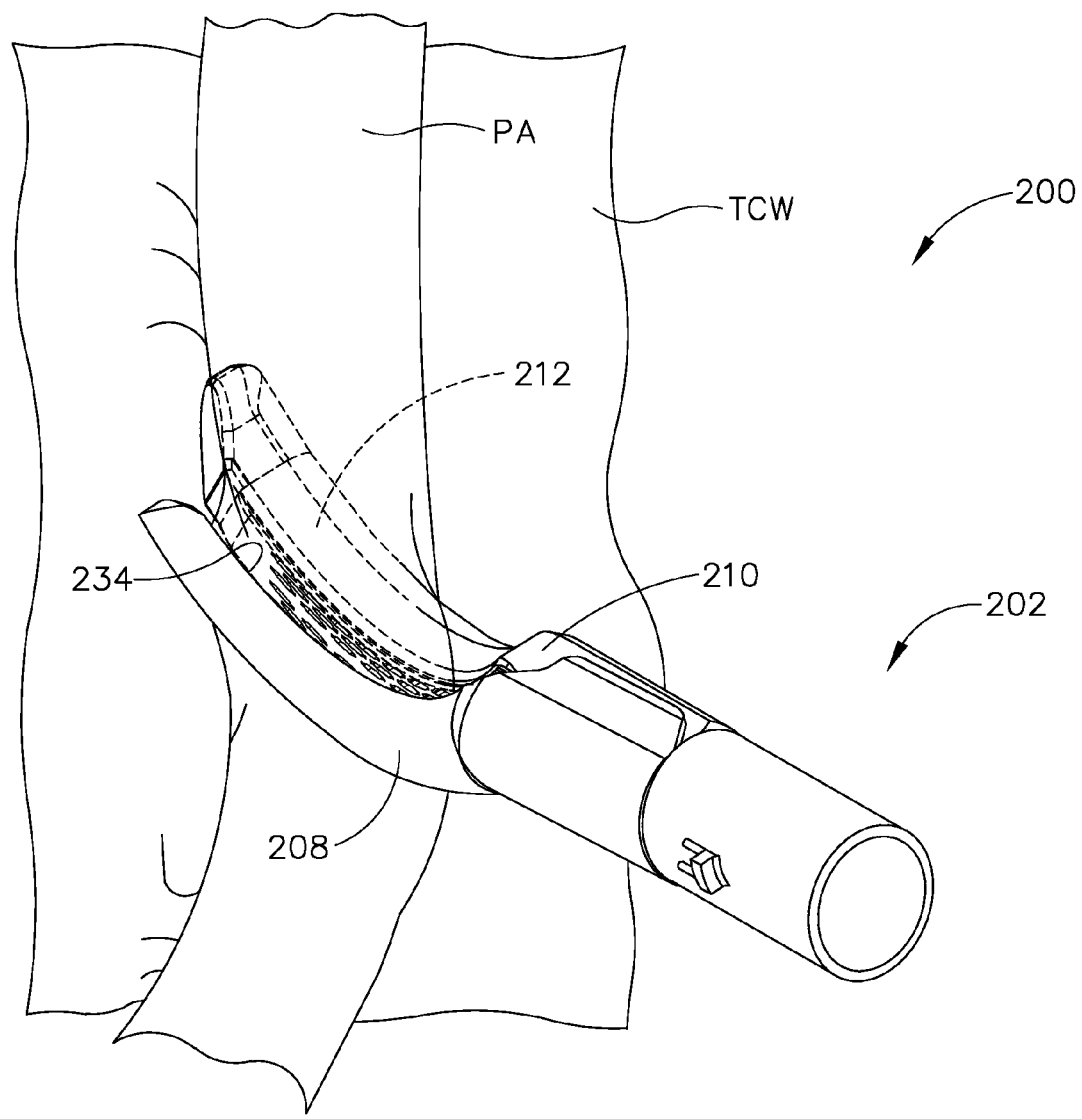
FIG. 11 is a perspective view of the endocutter of FIG. 10 illustrated in a closed configuration and positioned about a pulmonary artery.
Figure 12:
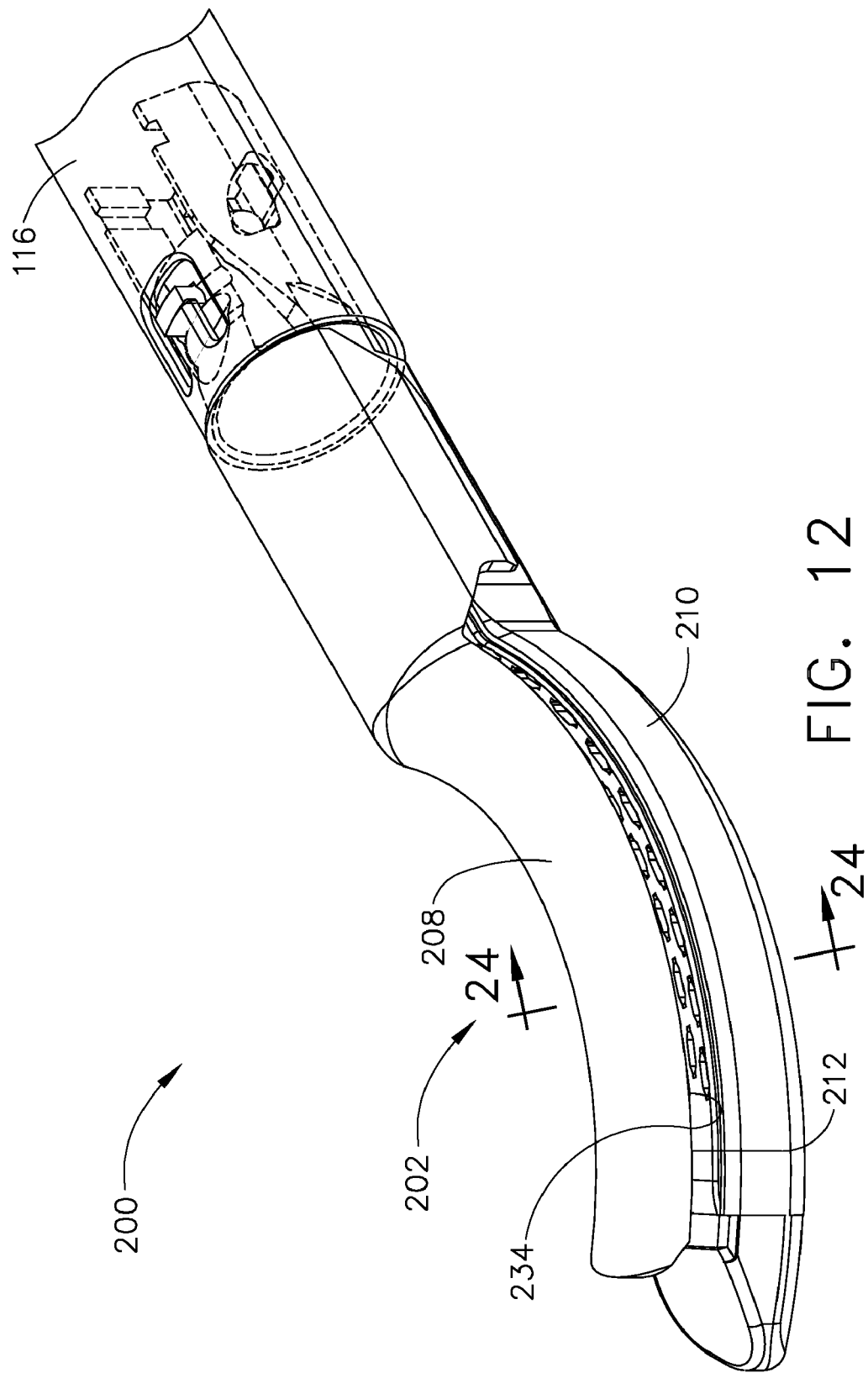
FIG. 12 is a perspective view of the end-effector of the endocutter of FIG. 11.

In various embodiments of the present invention, referring to FIG. 10, the end-effector of the endocutter is curved. A curved end-effector allows a surgeon to more easily position the end-effector against the curved wall of the thoracic cavity, for example. In at least one embodiment, the curvature of the end-effector can be configured to substantially match the contour of a typical thoracic cavity wall. In these embodiments, the curvature of several thoracic cavity walls can be measured and statistically analyzed to determine the optimum profile of the curved end-effector. This profile can include several arcuate portions and, in addition, several linear portions. In other embodiments, referring to endocutter 200 of FIGS. 10-14, the curvature of the thoracic cavity wall can be approximated by a single radius of curvature. Such embodiments can be simpler and less expensive to manufacture. In at least one embodiment, this radius of curvature is 1.2". In other various embodiments, the curvature of the end-effector can be configured to match the profile of the lower rectum, pelvis, or lower abdomen.

In order to transect the pulmonary artery PA, as mentioned above, a surgeon typically positions one of jaws 208 and 210 behind the pulmonary artery PA against the thoracic cavity wall TCW. Once positioned, referring to FIGS. 10 and 11, closure trigger 117 is actuated to pivot jaw 208 with respect to jaw 210 such that anvil 234 contacts the pulmonary artery and compresses the pulmonary artery between anvil 234 and staple cartridge 212. Unlike previous linear end-effectors, the curved profile of end-effector 202 assists the surgeon in locating the distal end of the end-effector with respect to the pulmonary artery. More particularly, referring to FIGS. 13 and 14, end 240 of jaw 210 can extend to one side of a centerline, or axis 242, defined by the distal end of shaft 106. As a result of this offset, the surgeon may be able to more readily see distal end 240 and evaluate whether the pulmonary artery is completely captured within the end-effector, for example.

Figure 15:
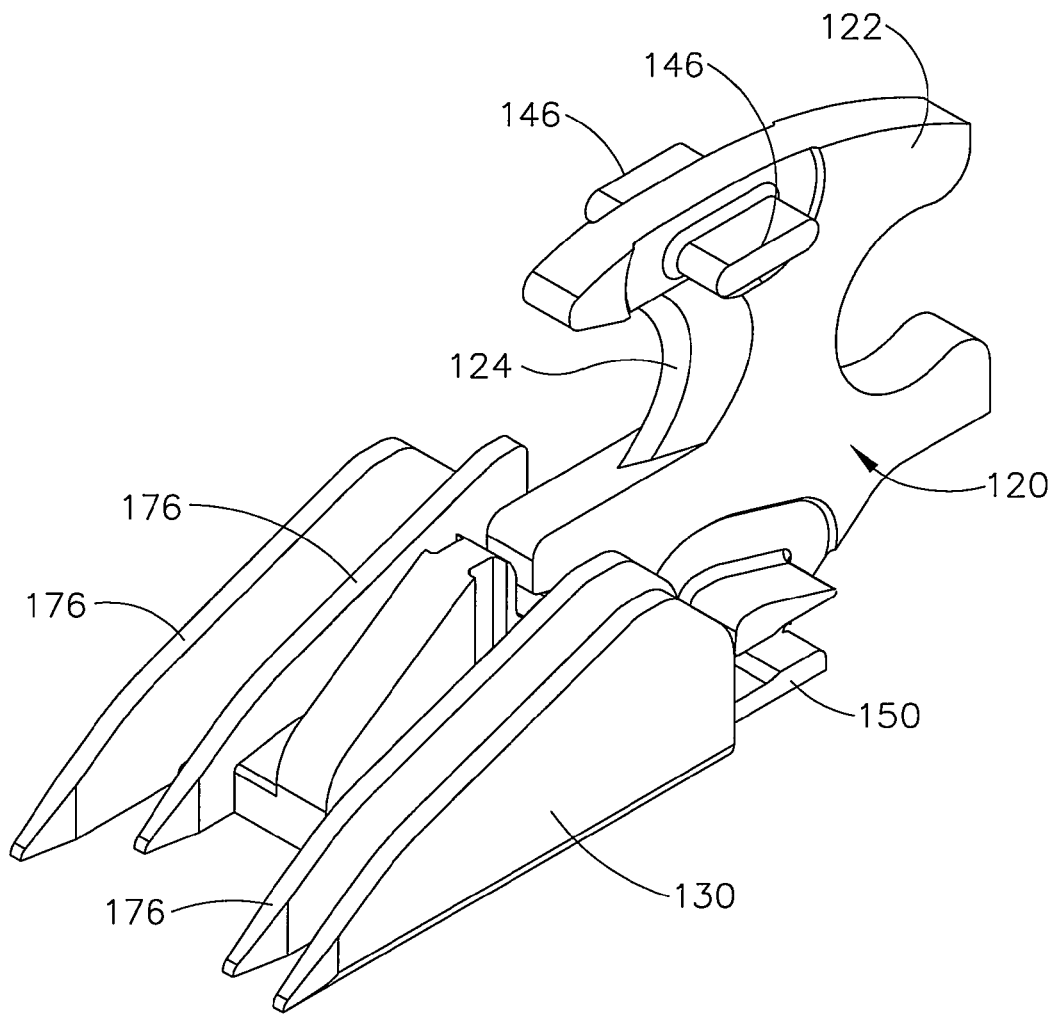
FIG. 15 is a perspective view of the cutting member and staple driver of the endocutter of FIG. 2.
Figure 16:
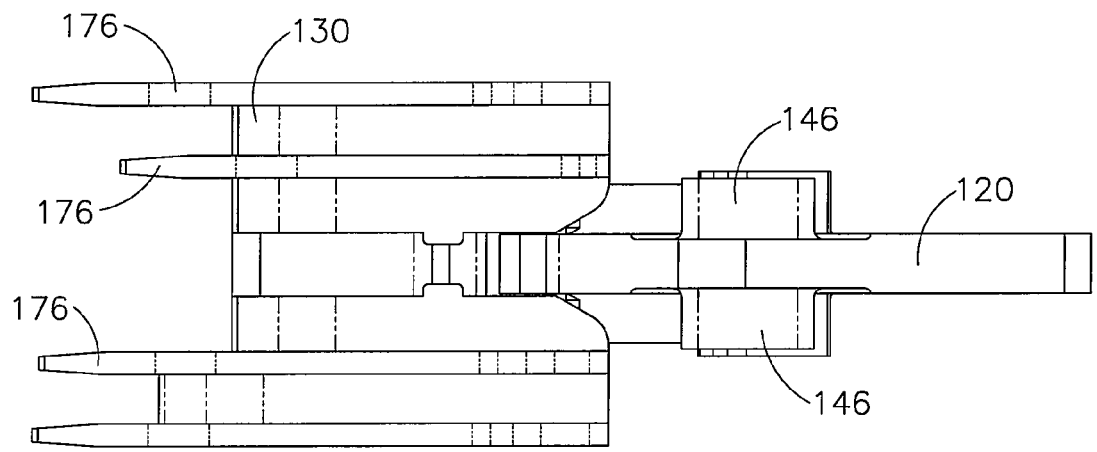
FIG. 16 is a top view of the cutting member and staple driver of FIG. 15.

Once the jaws of the endocutter have been closed, the cutting member of the endocutter can be advanced toward the tissue, as described above. In previous endocutters, referring to FIGS. 4, 15 and 16, cutting member 120 is configured to travel within linear slots defined by staple cartridge 112, staple cartridge channel 138, and anvil 134. Similarly, staple driver 130 is configured to travel within at least one linear slot defined by staple cartridge 112. As a result of these linear slots, cutting member 120 and staple driver 130 are moved in a straight line between the proximal and distal ends of the end-effector. For example, referring to FIG. 4, cutting member 120 includes first projections 146 extending from body 122 which are sized and configured to fit within slot 148 of anvil 134. Cutting member 120 further includes second projections 150 extending from body 122 which are sized and configured to retain cutting member body 122 within slot 164 of staple cartridge 112 and slot 152 of jaw 110. Accordingly, as cutting member 120 is advanced from the proximal end of the end-effector to the distal end, linear slots 148, 152 and 164 define a linear path for cutting member 120.

Figures 13, 14:
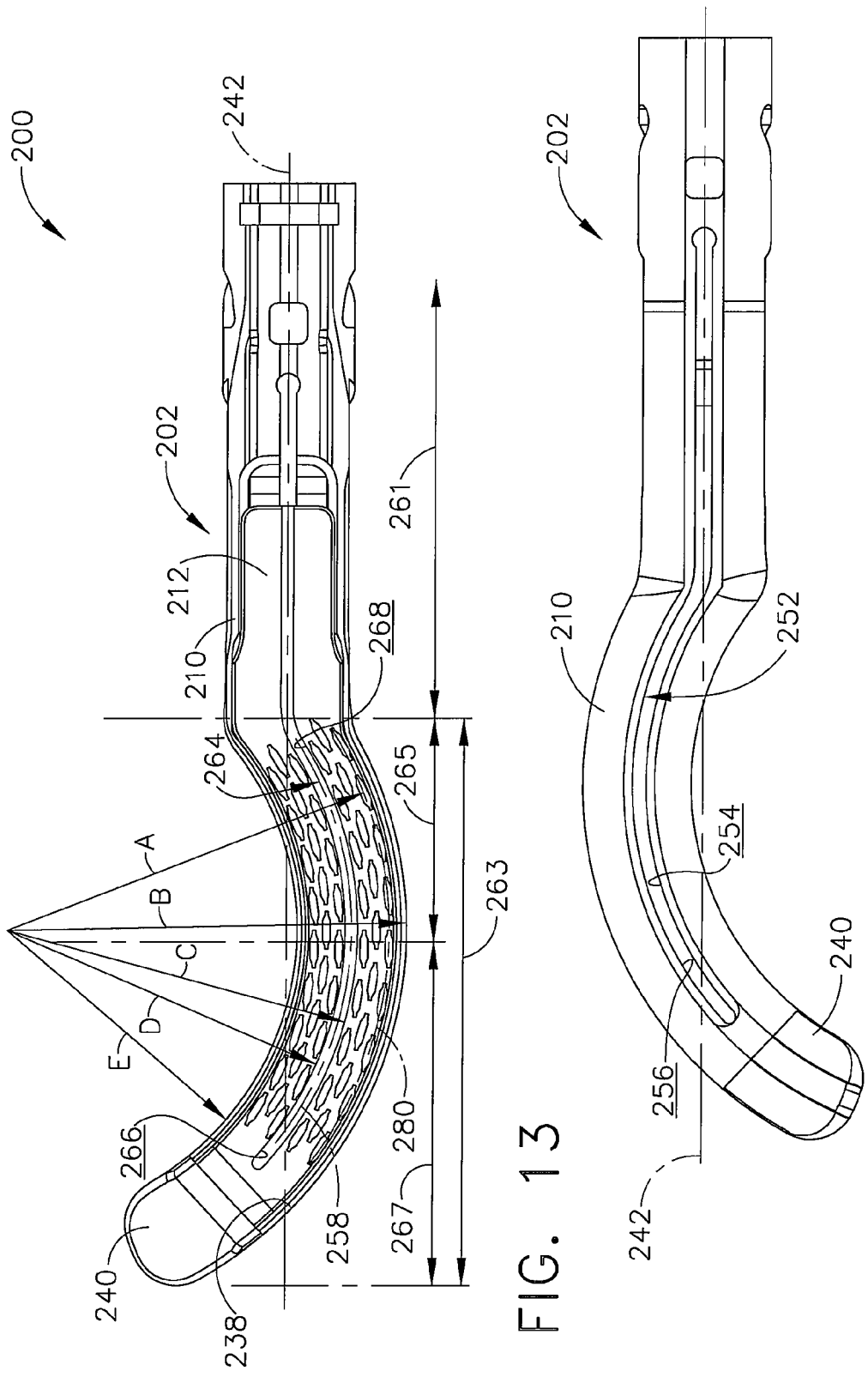
FIG. 13 is a top view of the staple cartridge of the end-effector of FIG. 12.
FIG. 14 is a bottom view of the jaw configured to support the staple cartridge of FIG. 13.

In various embodiments of the present invention, referring to FIGS. 13 and 14, staple cartridge 212, staple cartridge channel 238 and anvil 234 can include curved slots for controlling the movement of cutting member 120 and staple driver 130 along a curved path. These curved slots can include several arcuate portions and several linear portions. In various embodiments, the curved slots can be defined by one radius of curvature. In the embodiment illustrated in FIGS. 13 and 14, staple cartridge 212 and staple cartridge channel 238 can include curved slots 264 and 252, respectively. Similar to the above, curved slots 264 and 252 can be configured to receive a portion of cutting member 120 and guide cutting member 120 along a path defined by slots 264 and 252. However, owing to the substantially linear configuration of cutting member 120, cutting member 120 may, in some circumstances, become misaligned or stuck within curved slots 264 and 252, or a corresponding curved slot in anvil 234.

Figure 17:
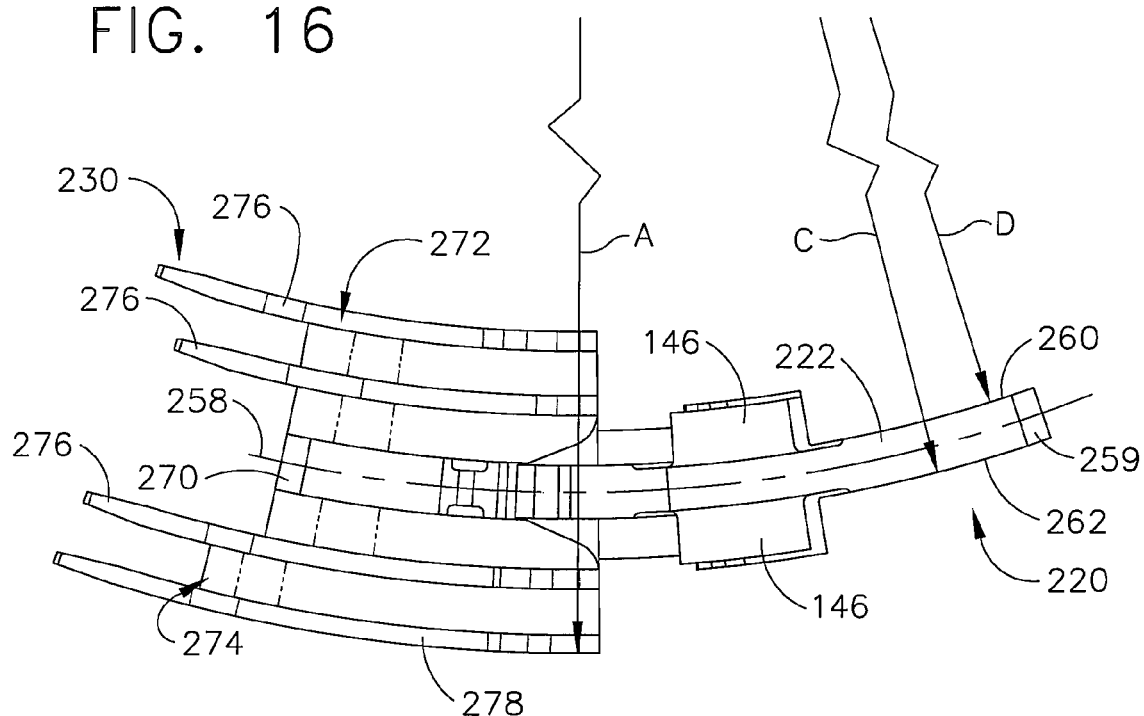
FIG. 17 is a top view of a cutting member and staple driver in accordance with an embodiment of the present invention.
Figure 20:
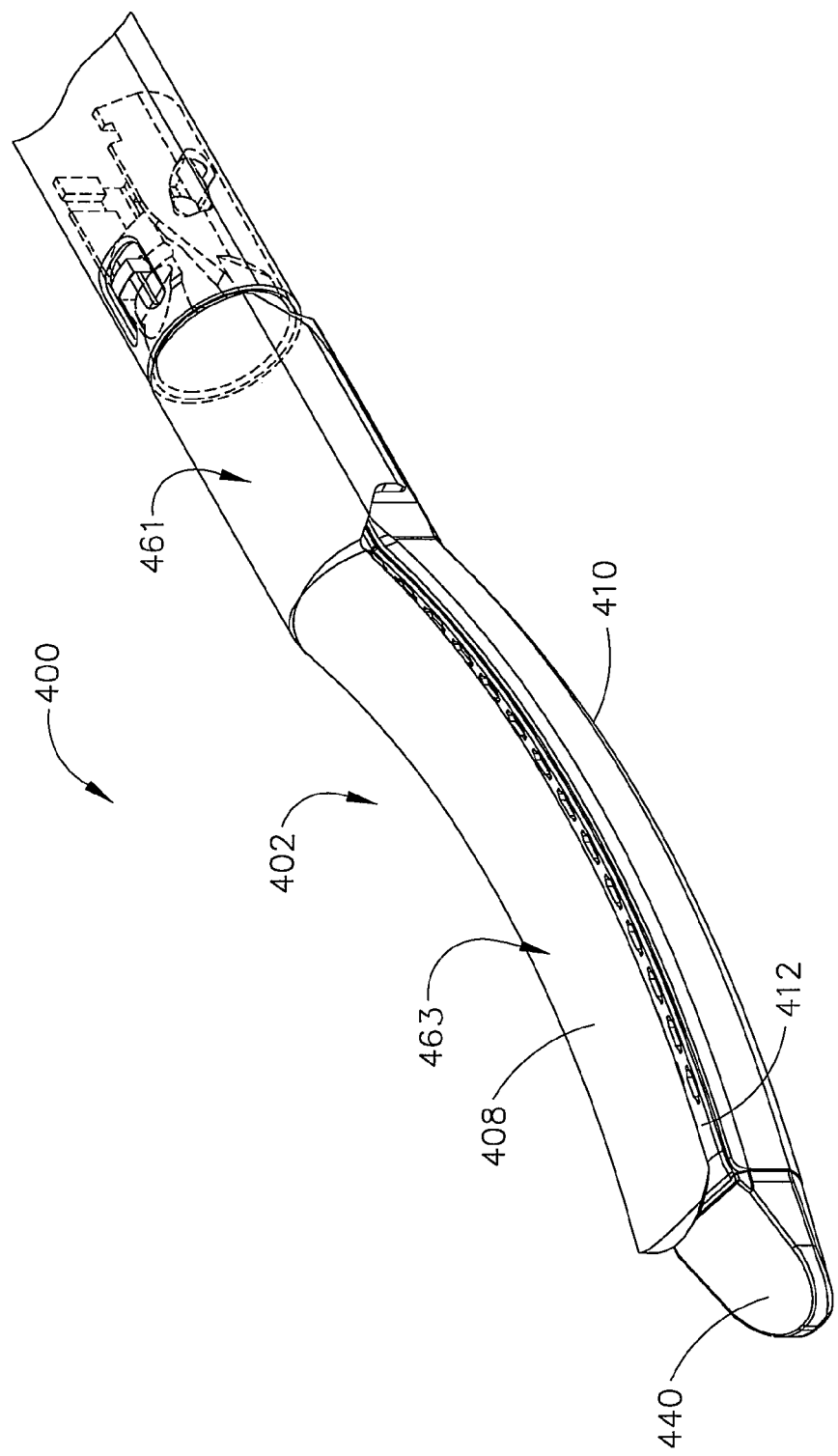
FIG. 20 is a perspective view of an endocutter having a curved end-effector in accordance with an alternative embodiment of the present invention.
Figure 21:
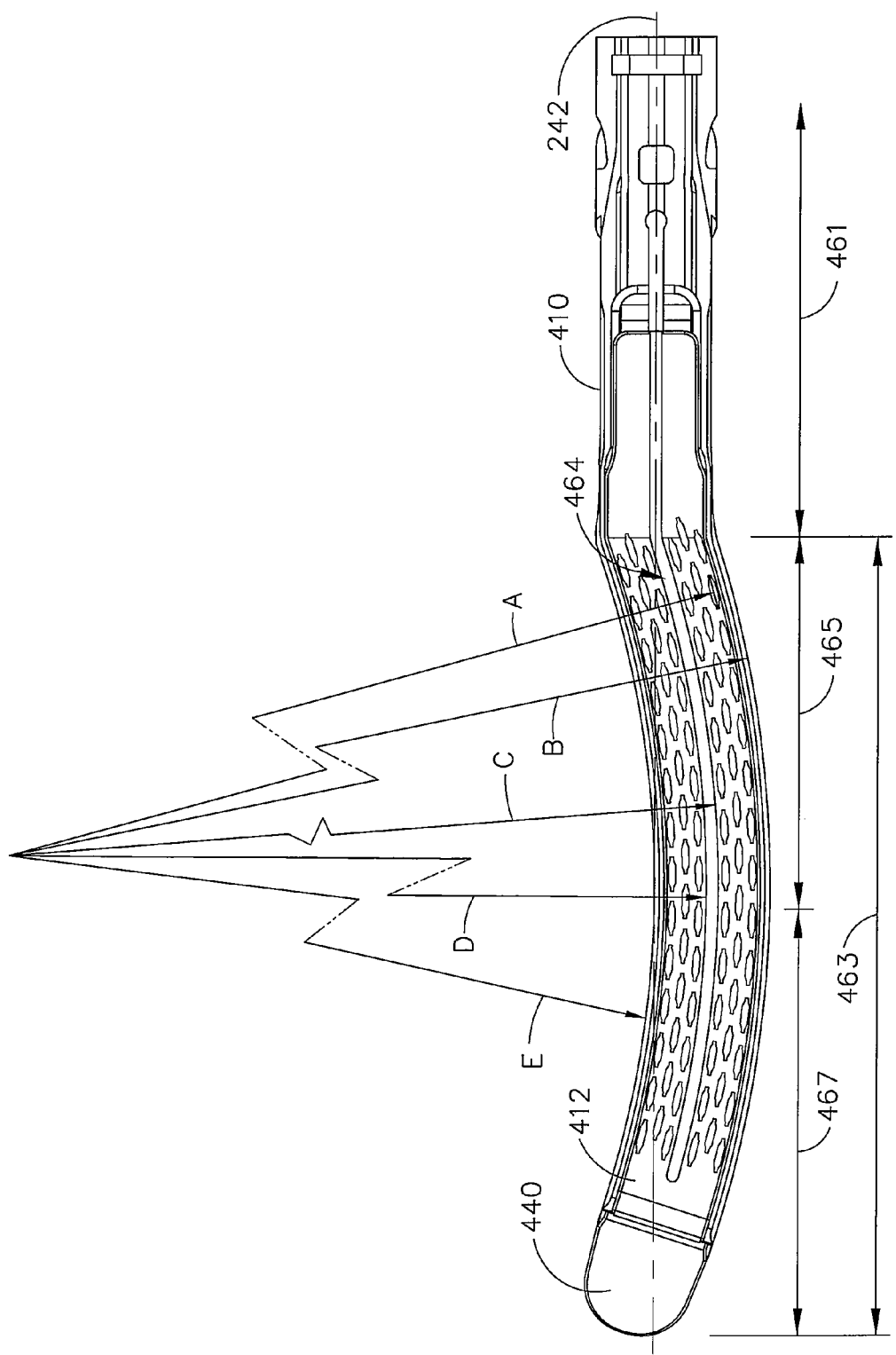
FIG. 21 is a top view of the staple cartridge of the end-effector of FIG. 20.

To ameliorate the above-described problem, at least a portion of the cutting member and staple driver can be curved. In at least one embodiment, the cutting member and staple driver can be configured to substantially match the curvature of the path defined by curved slots 264 and 252, i.e., path 258. More particularly, referring to FIGS. 13 and 17, cutting member body 222 can include a center portion which is configured to match the radius of curvature of path 258, and a curved inner portion 260 and a curved outer portion 262 which are configured to co-operate with the sidewalls of curved slots 264 and 252. For example, curved cartridge channel slot 252 can include inner surface 254 and outer surface 256 and curved staple cartridge slot 264 can include inner surface 266 and outer surface 268 where, in the present embodiment, inner surfaces 254 and 266 are substantially defined by radius of curvature D, which is smaller than the radius of curvature of path 258, and outer surfaces 256 and 268 are substantially defined by radius of curvature C, which is larger than the radius of curvature of path 258. As illustrated in FIG. 17, inner portion 260 of cutting member 220 can be configured to closely parallel the profile of inner surfaces 254 and 266, and outer portion 262 of cutting member 220 can be configured to closely parallel the profile of outer surfaces 256 and 268. Furthermore, although not illustrated, anvil 234 can include a curved slot which, similar to slots 264 and 252, co-operates with curved cutting member 220 to guide cutting member along path 258. As a result of the above, the likelihood of cutting member 220 becoming misaligned or stuck within curved path 252 can be reduced.

Alternatively, although not illustrated, the cutting member can include slots which are configured to co-operate with features on the anvil and/or staple cartridge and guide the cutting member along a curved path. More particularly, the anvil and/or staple cartridge can each include an elongate, arcuate projection, or a plurality of projections, which define a curved, or curvilinear, path for the cutting member. The slots of the cutting member can be configured to receive the projections and guide the cutting member along the curved path. In one embodiment, one of the anvil and staple cartridge can include such a projection, or a plurality of projections, and the other of the anvil and staple cartridge can include a slot configured to receive a portion of the cutting member, as described above.

Similar to the above, at least a portion of staple driver 230 can be configured to substantially match the curvature of path 258. More particularly, referring to FIG. 17, staple driver 230 can include a center arcuate portion 270 which is configured to match the radius of curvature of path 258, and an inner arcuate portion 272 and an outer arcuate portion 274 which are configured to co-operate with the sidewalls of slots, or channels, within staple cartridge 212. Similar to staple driver 130, staple driver 230 can include ramps which are configured to lift, or deploy, staples 132 against anvil 234 positioned opposite staple cartridge 212. However, in the present embodiment, ramps 276 of staple driver 230 can be curved to deploy staples 132 along a curved staple line. More particularly, for example, the ramps can be defined by a radius of curvature which substantially matches the radius of curvature of a staple line. For example, ramp 278 is defined by a radius of curvature which substantially matches the radius of curvature of staple line 280, i.e., radius of curvature A.

Although the path of the cutting member has been described above as being defined by a single radius of curvature, the invention is not so limited. In various embodiments, referring to FIGS. 13 and 14, end-effector 202 of endocutter 200 can include curved portion 263 and, in addition, linear portion 261 which is substantially collinear with an axis defined by the distal portion of shaft 116, i.e., axis 242. In at least one embodiment, curved portion 263 can further include first portion 265 and second portion 267. Referring to FIG. 13, first portion 265 can include a proximal end connected to linear portion 261 positioned along axis 242 and a distal end spaced from axis 242 wherein second portion 267 can include a proximal end connected to the distal end of first portion 265 and extend toward axis 242. Stated another way, first portion 265 can define an arcuate portion which extends away from axis 242 and second portion 267 can define an arcuate portion which extends toward axis 242. As described above, an end-effector having such a profile may facilitate the positioning of the end-effector against the wall of the thoracic cavity, for example.

Referring to FIGS. 18-21, the end-effector of other various embodiments of the present invention can include other advantageous profiles. For example, referring to FIGS. 18 and 19, end-effector 302 can include linear portion 361 and curved portion 363 wherein the distal end of slot 364 can be positioned along axis 242. As a result, although the cutting member progresses along an arcuate path offset with respect to axis 242, the cutting member will stop at a point along axis 242. Thus, as long as the surgeon is able to discern the orientation of axis 242, the surgeon will know that the cutting member will not progress beyond axis 242 and can thereby gauge the point at which the tissue will no longer be transected. In another embodiment, referring to FIGS. 20 and 21, end-effector 402 can include linear portion 461 and curved portion 463 wherein distal tip 440 of the end-effector lies along axis 242 although at least a portion of the end-effector is offset with respect to axis 242. In this embodiment, as long as the surgeon is able to discern the orientation of axis 242, the surgeon can gauge the location of the distal end of the end-effector when moving or dissecting tissue.

In other various embodiments, referring to FIGS. 22 and 23, the end-effector can define an arcuate path for the cutting member that is defined by an angle that is greater than or equal to 90 degrees. More particularly, for example, path 558 can include linear portion 561 and curved portion 563 wherein curved portion 563 is defined by a radius of curvature that spans an arc corresponding to an approximately 110 degree angle. As a result of the significant curvature of curved portion 563, a surgeon can position a pulmonary artery, for example, entirely within curved portion 563. In various embodiments, referring to FIG. 26, staples 132 may only be positioned within cavities in curved portion 563, and not linear portion 561. In these embodiments, the staple lines can be comprised of continuous, curved rows without abrupt changes in direction within the staple line. As known in the art, abrupt changes in a staple line may provide a leak path for blood to flow therethrough. As a result of the above embodiments, the likelihood of such a leak path is reduced.

As described above, the anvil and staple cartridge can include curved slots for receiving and guiding the cutting member. In many embodiments, the anvil and the staple cartridge can be configured such that their features parallel the curved slots therein. For example, referring to FIGS. 13 and 14, curved portion 263 of staple cartridge 212 can include an inner radius of curvature and an outer radius of curvature which parallel the radius of curvature of curved slot 264. More particularly, referring to FIG. 13, the inner surface of staple cartridge 212 can be defined by radius of curvature E and the outer surface of staple cartridge 212 can be defined by radius of curvature B, wherein curvatures B and E share a substantially common radial point with radius of curvatures C and D which, as described above, substantially define the inner and outer surfaces of slot 264. However, in various embodiments, although not illustrated, the inner and outer surfaces of the anvil and/or staple cartridge, or any other features thereof, may be non-parallel to the curved slot. In these embodiments, the anvil and staple cartridge, and the jaws surrounding them, may be configured to achieve any suitable configuration or purpose.

In previous endocutters, as described above and referring to FIGS. 4 and 8, linear drive bar 126 is configured to advance cutting member 120 along a linear path and, as a result, drive bar 126 is constructed such that is rigid and does not substantially deflect. After cutting member 120 has been advanced into slots 148, 164 and 152 of anvil 134, staple cartridge 112, and staple cartridge channel 138, respectively, at least a portion of drive bar 126 can enter into slots 148, 164 and 152. However, although cutting member 120 is guided and supported within slots 148, 164, and 152, drive bar 126, in these previous devices, is unsupported within slots 148, 164, and 152. As a result, drive bar 126 may deflect or buckle in an uncontrollable and undesirable manner when load is transmitted therethrough.

Figure 25:
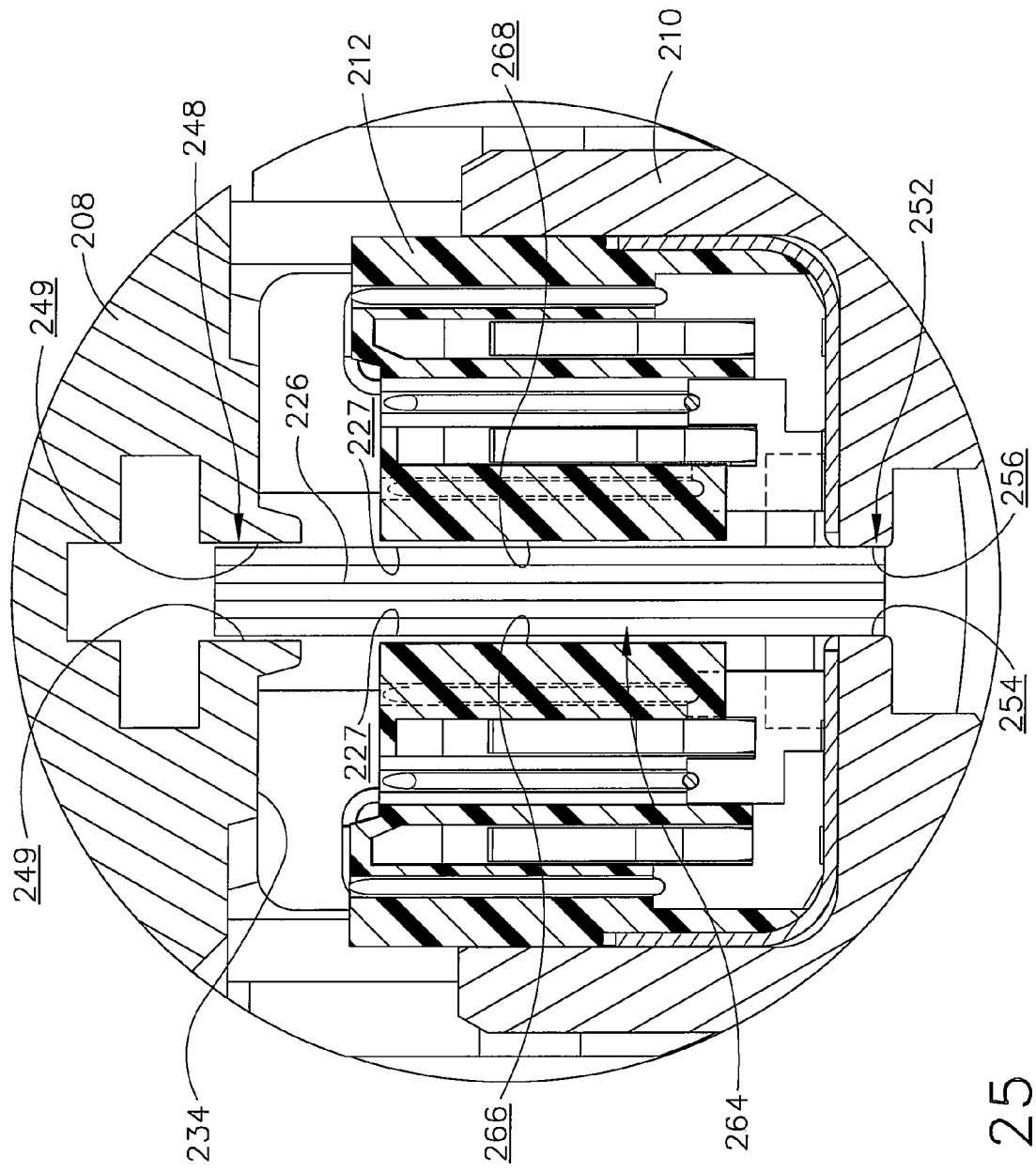
FIG. 25 is a cross-sectional view of the end-effector of FIG. 12 after the drive bar has been advanced into the end-effector.

In various embodiments of the present invention, a flexible drive bar can be used to advance the cutting member within the end-effector. More particularly, in order for the drive bar to be advanced into and translate within the curved slots of the end-effector, the drive bar can deflect to closely parallel the curvature of the curved slots of the end-effector. In various embodiments, unlike previous endocutters, the slots within the anvil and staple cartridge can be configured to support the flexible driver bar. More particularly, after cutting member 120 has been at least partially advanced within slots 248, 264, and 252, referring to FIG. 25, at least a portion of drive bar 226 can enter slots 248, 264, and 252. Slot 248 can include support surfaces 249 which are configured to abut, or be positioned closely adjacent to, side surfaces 227 of drive bar 226. Similarly, surfaces 254 and 256 of slot 252 and surfaces 266 and 268 of slot 264 can also support the drive bar. While these features are particularly advantageous when used with curved end-effectors, they can also be used in linear end-effectors. In these embodiments, even though the slots may be linear, the slots can support the driver, whether rigid or flexible, and prevent it from buckling in the event that it is overloaded, for example.

Although flexible drive bar 226 can be used to advance linear cutting member 120 and linear staple driver 130 within a curved end-effector, as described above, flexible drive bar 226 can also be used to advance curved cutting members and staple drivers, such as cutting member 220 and staple driver 230, for example, within a curved end-effector. Furthermore, although not illustrated, one of the anvil and staple cartridge can include a slot configured to receive and guide the cutting member and the other of the anvil and staple cartridge can include a slot configured to receive and support the drive bar. In these embodiments, the slot which is configured to receive the cutting member can have a different geometry than the slot which is configured to receive the drive bar. Accordingly, the cutting member and the drive bar can have different thicknesses, for example.

In various embodiments, the support surfaces of slots 248, 264 and 252 may be continuous, i.e., they may be configured to contact drive bar 226 continuously along the length thereof, or, alternatively, slots 248, 264 and 252 may be configured to contact drive bar 226 at various, spaced-apart locations. In these embodiments, projections may extend from the slot walls to define the path of the cutting member and the drive bar. In various embodiments, drive bar 226 may be comprised of a flexible, unitary material such as plastic, for example. Alternatively, referring to FIGS. 25 and 26, drive bar 226 may be comprised of a laminated material, i.e., a material comprised of two or more materials bonded together. In these embodiments, two or more strips of material may be glued together where the strips have the same cross-sectional geometry, or, alternatively, different cross-sectional geometries. Furthermore, the strips may be comprised of the same material or different materials. The cross-sectional geometries and materials of the above-described embodiments may be selected such that the drive bar is more flexible when deflected in one direction and less flexible when deflected in a different direction.

As described above, the curvature of an end-effector can be selected such that it facilitates the placement of the end-effector in a particular surgical site. In various embodiments, referring to FIGS. 35-37 and 38-40, the end-effector can be curved in a downward or upward direction, i.e., it can be curved in a plane that is substantially parallel to planes defined by the staple lines. More particularly, referring to FIGS. 38 and 39, staple cavities 803, which are configured to store staples 132 therein, are positioned along staple lines 805 and 807, for example, such that staples 132, when they are deployed from staple cartridge 812, are deployed in substantially parallel planes which are at least partially defined by staple lines 805 and 807.

Figure 35:
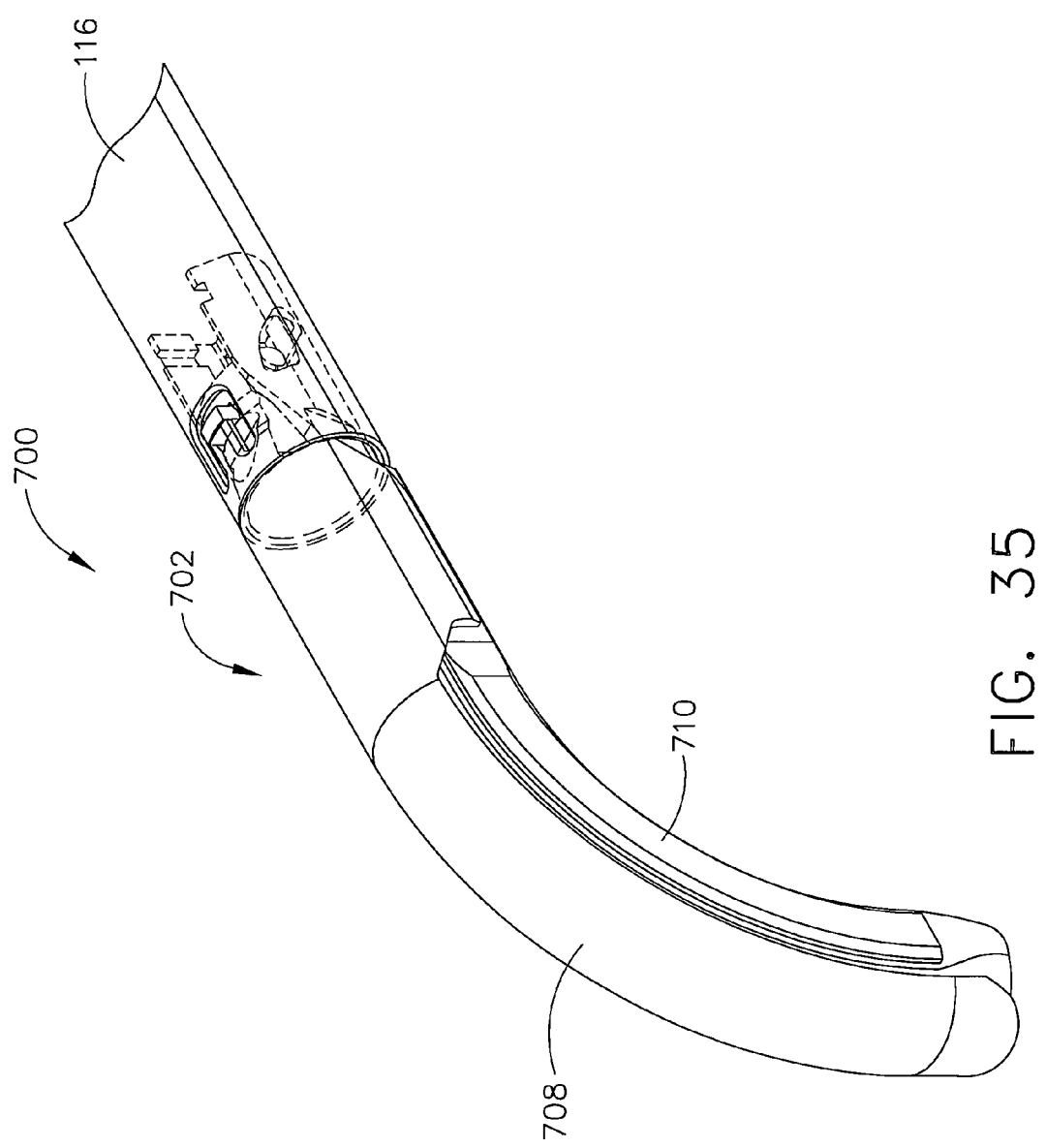
FIG. 35 is a perspective view of an endocutter having a curved end-effector in accordance with an alternative embodiment of the present invention.
Figure 36:
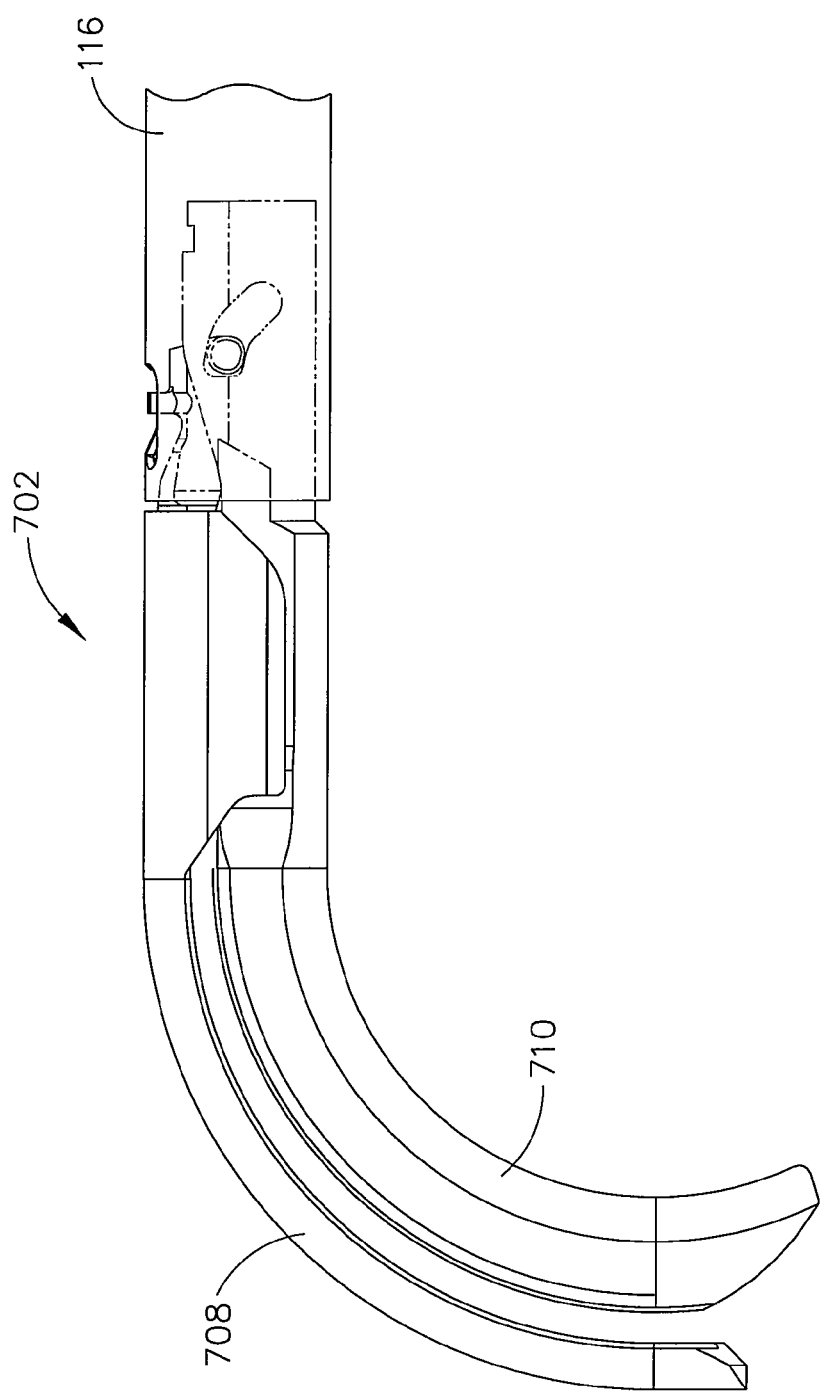
FIG. 36 is a side view of the endocutter of FIG. 35.
Figure 37:
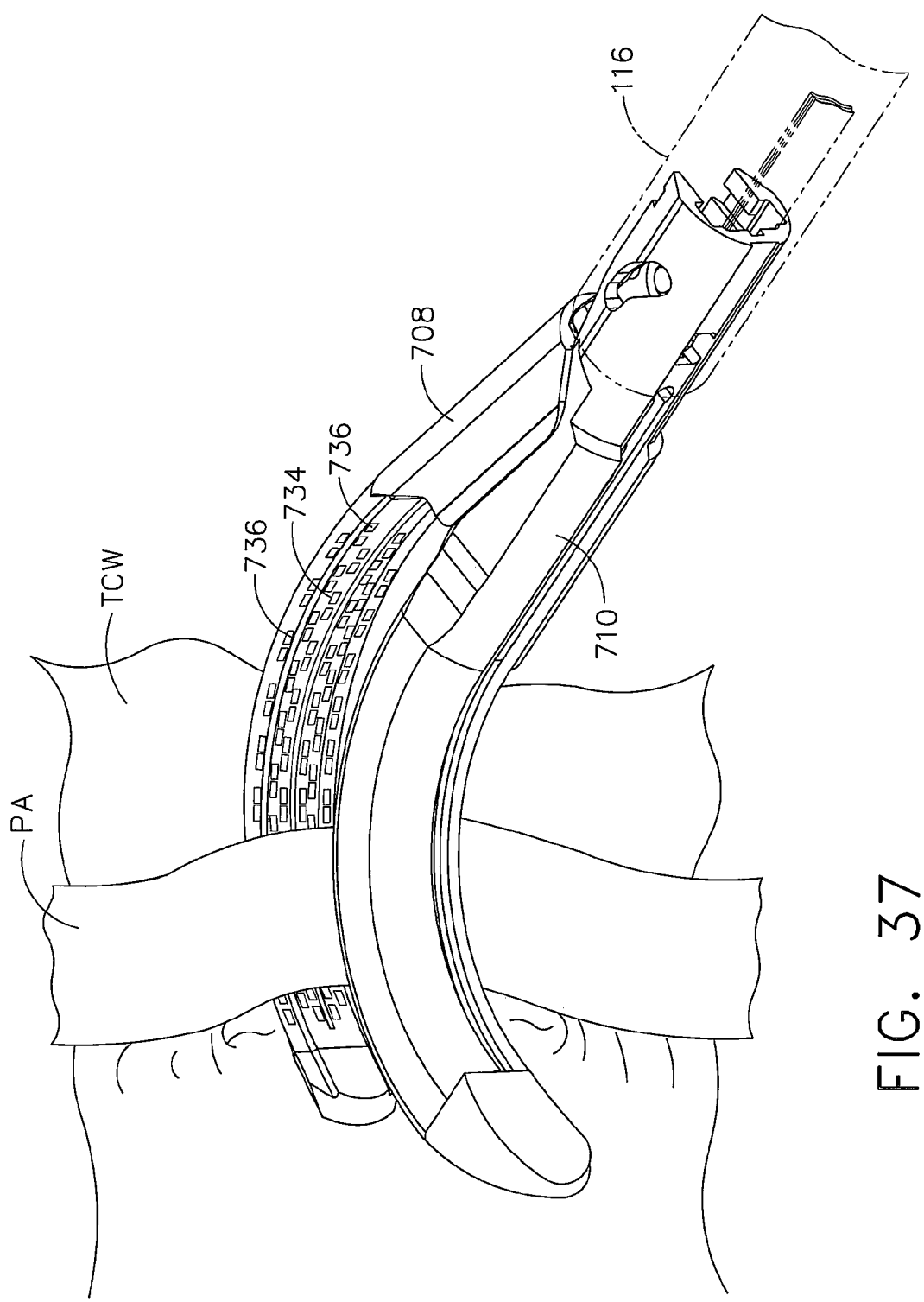
FIG. 37 is a schematic of the endocutter of FIG. 35 being used to transect a pulmonary artery.
Figure 40:
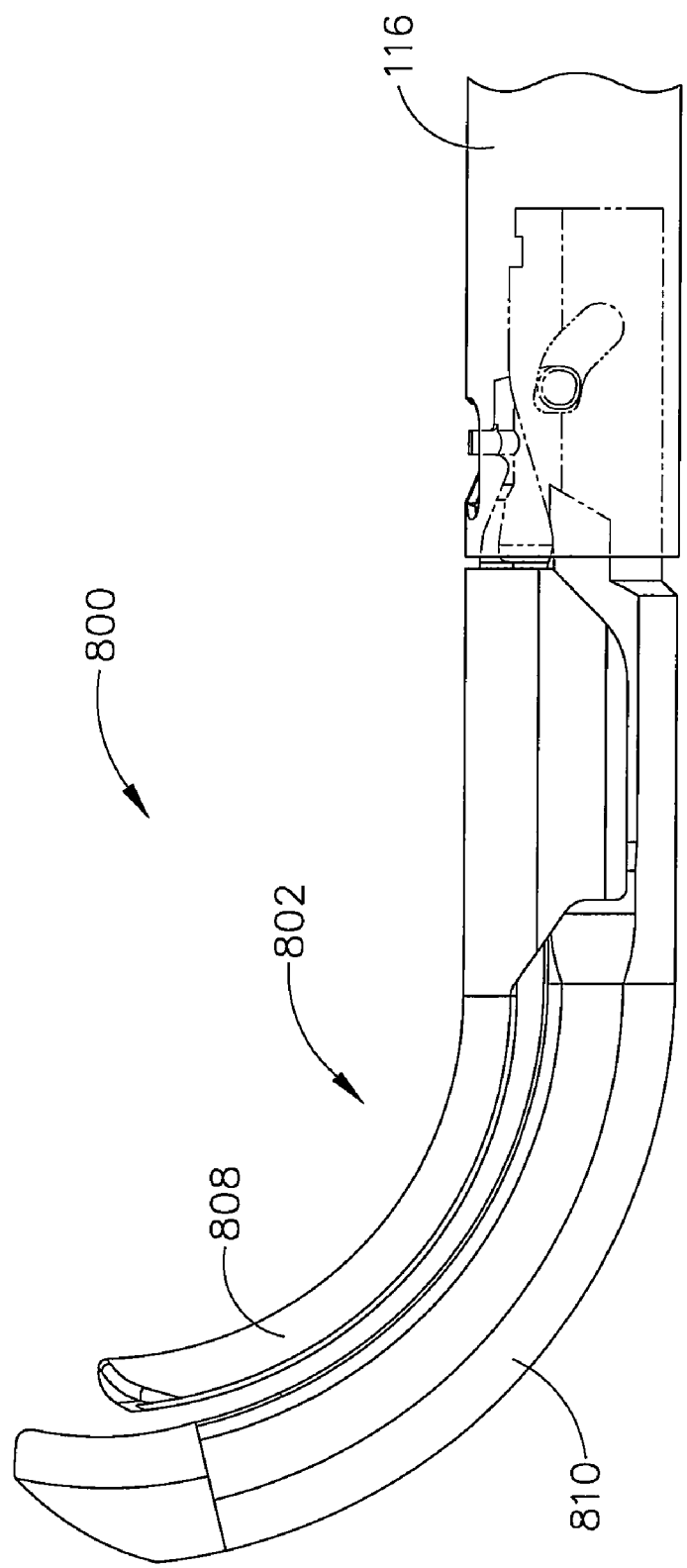
FIG. 40 is a side view of the end-effector of the endocutter of FIG. 39.

For each parallel plane described above, as a result of these upward and/or downward curvatures, staples 132 can be deployed along axes which are co-planar, but not parallel. More particularly, referring to FIG. 39, a first staple 132 (not illustrated in FIG. 39) can be deployed from its staple cavity 803 along axis 853 and a second staple 132 can be deployed from its staple cavity 803 along axis 855. While axis 853 and axis 855 can be co-planar, as illustrated in FIG. 39, axis 853 and axis 855 are not parallel. In some embodiments, the axes defined by staple cavities 803 can converge, as illustrated in FIGS. 38 and 39, or diverge, as illustrated in FIGS. 35-37. In various embodiments, the staple deployment axes can define an angle therebetween which is greater than or equal to 30 degrees. In other various embodiments, the axes can be substantially perpendicular and, in further embodiments, the axes can define an angle that is greater than ninety degrees.

Figure 24:
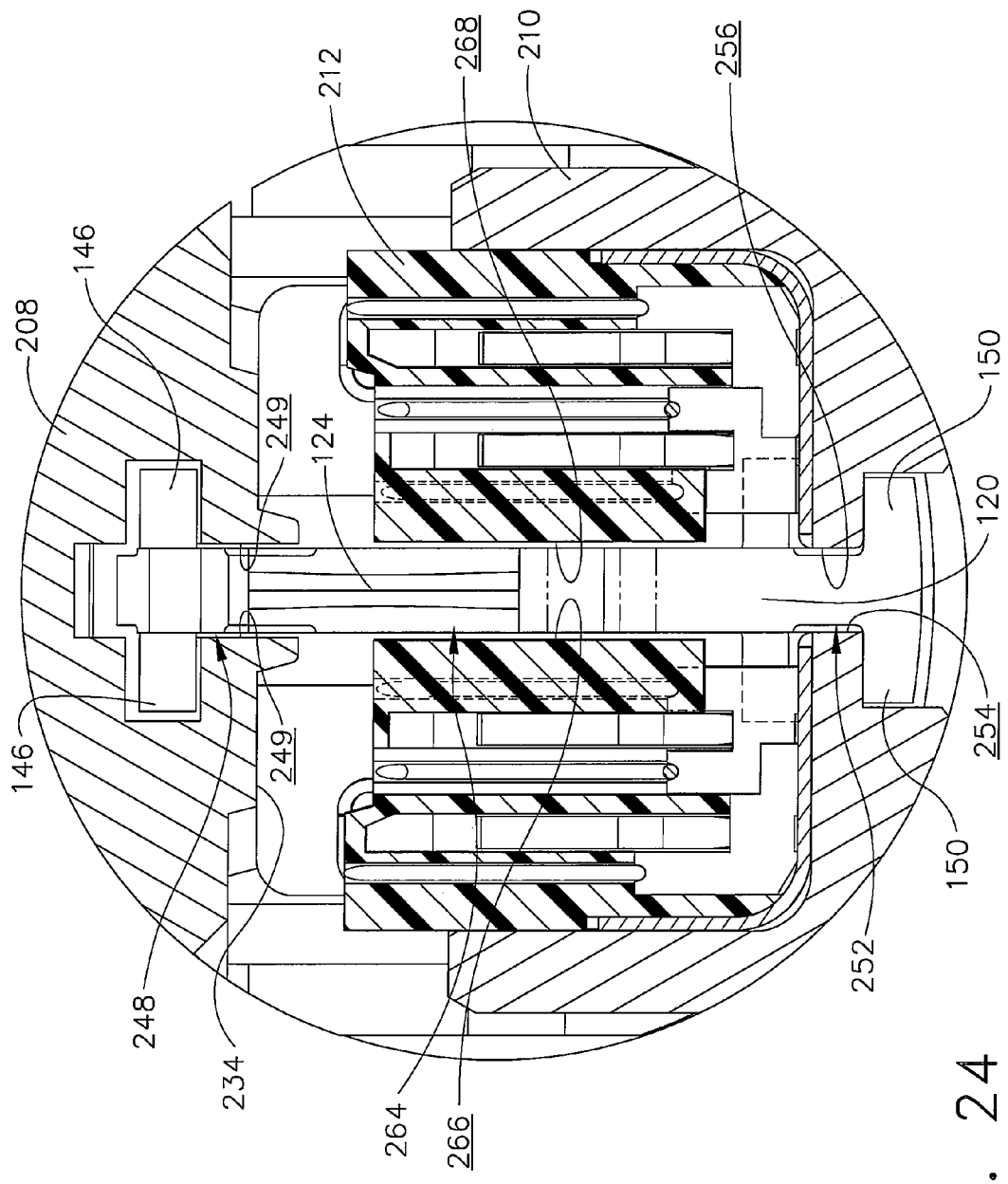
FIG. 24 is a cross-sectional view of the end-effector of FIG. 12 taken along line 24-24 in FIG. 12.
Figure 26:
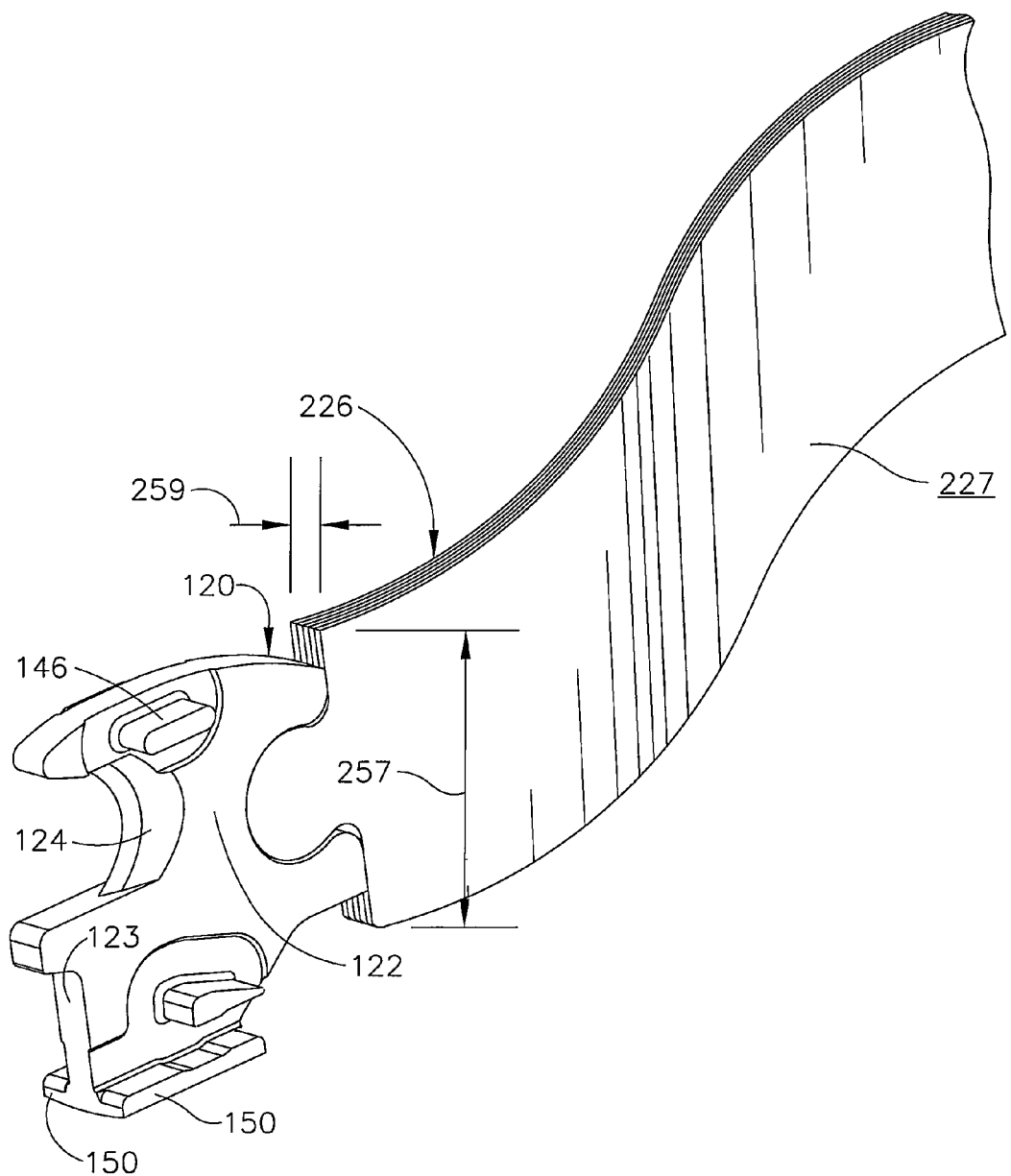
FIG. 26 is a schematic of the cutting member and drive bar of the endocutter of FIGS. 24 and 25.

As described above, an endocutter in accordance with an embodiment of the present invention can include a cutting member which is advanced through and guided by curved slots in the staple cartridge and/or anvil. For example, referring to FIGS. 38-43, staple cartridge 812 can include slot 864 which is configured to receive and guide cutting member 120. Similar to the above, endocutter 800 can further include a drive bar for advancing cutting member 120 within slot 864 of staple cartridge 812, however, owing to the direction and degree of the curvature of staple cartridge 812, some drive bars may be largely unsuitable for use with endocutter 700 or 800, for example. More particularly, the illustrated drive bars 126 and 226 in FIGS. 4 and 24, respectively, owing to their cross-sectional geometries, may not be particularly well-suited to flex in a substantially downward or substantially upward direction as required by endocutters 700 and 800, respectively. Referring to FIG. 26, for example, the illustrated cross-section of drive bar 226 is substantially rectangular and is defined by height 257 and width 259. As illustrated in FIG. 26, height 257 is substantially greater than width 259 and, as a result, the cross-section of the illustrated drive bar 226 has a moment of inertia with respect to height 257 that is substantially greater than the moment of inertia with respect to width 259. Accordingly, the illustrated drive bar 226 is substantially less flexible with respect to height 257 than width 259 and may not be able to sufficiently bend in the substantially downward and upward directions described above. It is important to note that drive bars 126 and 226 are not limited to the configurations described above. On the contrary, drive bars 126 and 226 can have cross-sections in which the width is greater than the height. Any reference in this paragraph to drive bars 126 and 226 are references to the particular drive bars 126 and 226 that happen to be illustrated in FIGS. 4 and 24, respectively.

Figure 41:
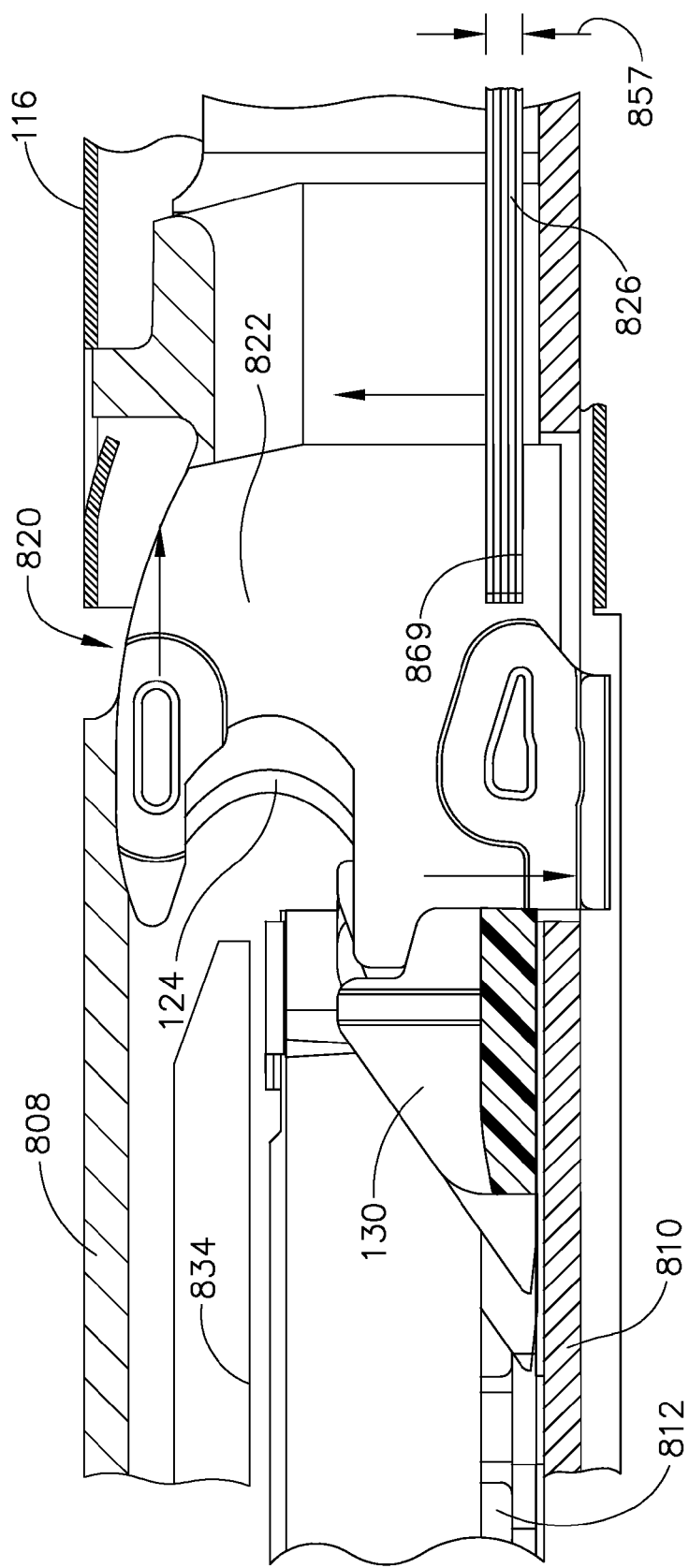
FIG. 41 is a partial cross-sectional view of the end-effector of the endocutter of FIG. 38.
Figure 42:
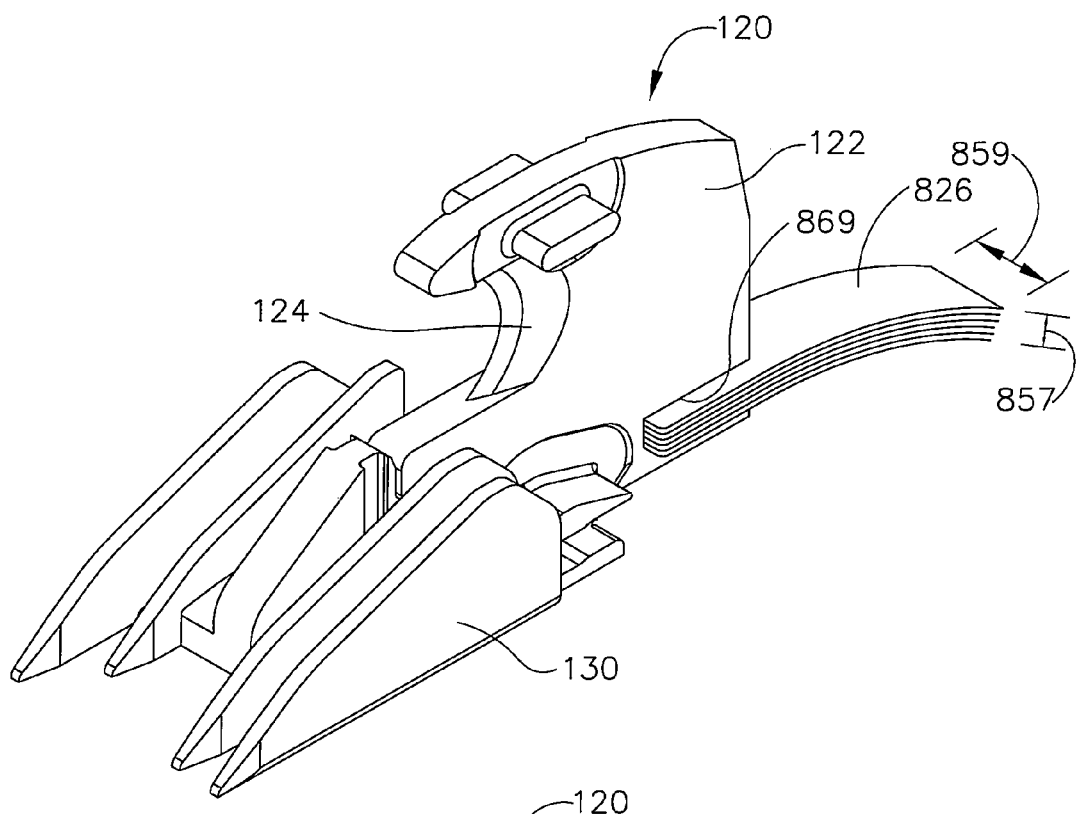
FIG. 42 is a perspective view of the staple driver, cutting member and drive bar of FIG. 41.
Figure 43:
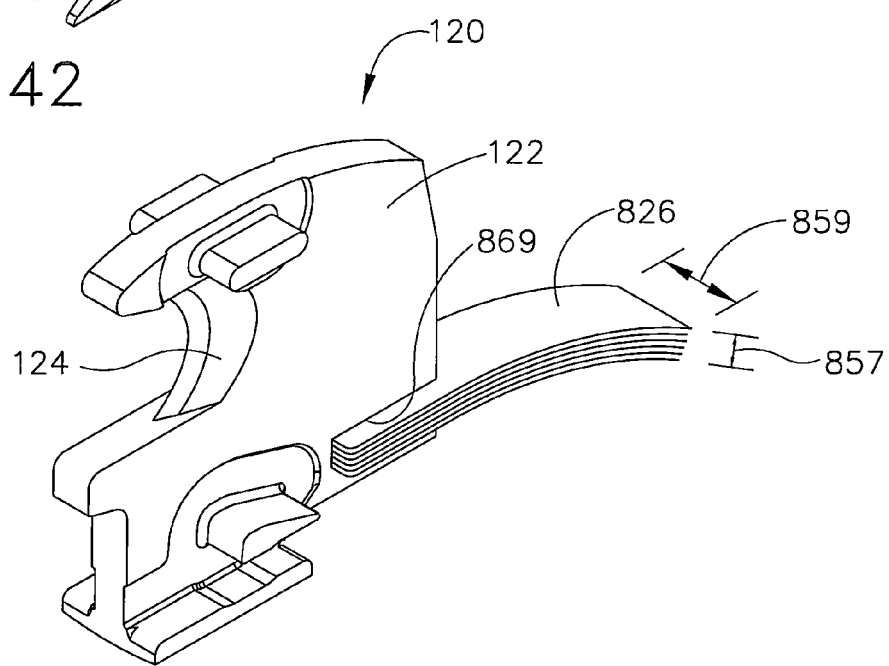
FIG. 43 is a perspective view of the cutting member and drive bar of FIG. 41.
Figure 44:
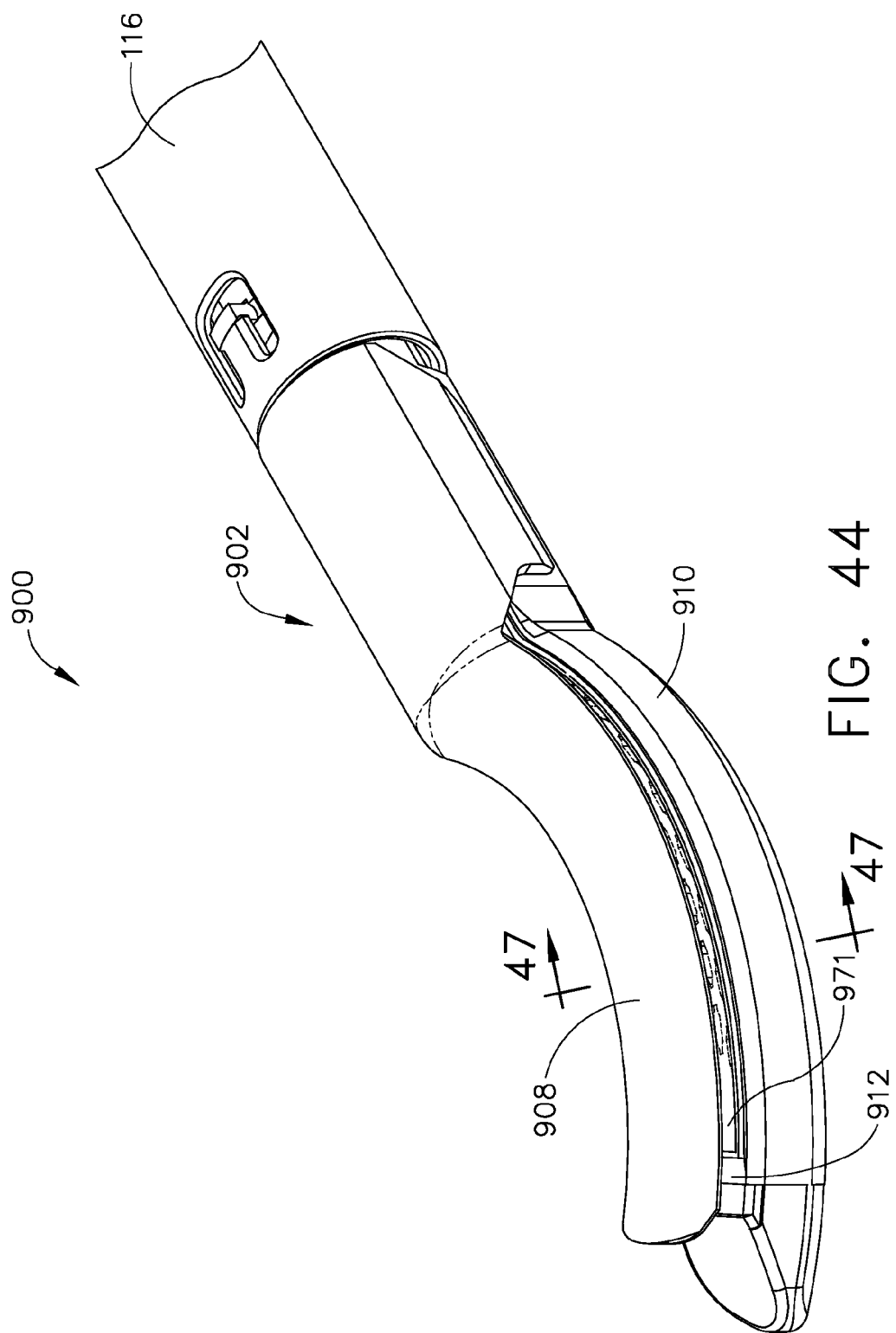
FIG. 44 is a perspective view of an endocutter having a curved staple cartridge and a curved anvil configured to retain buttress material thereon in accordance with an embodiment of the present invention.

Referring to FIGS. 41-43, endocutter 800 can include drive bar 826 which, similar to drive bar 226, is configured to advance cutting member 120, or a curved cutting member, through curved slots in an end-effector. In various embodiments, drive bar 826 can include a cross-sectional geometry having a width 859 that is greater than its height 857. In these embodiments, the moment of inertia of the cross-section with respect to height 857 is less than the moment of inertia with respect to width 859. As a result, drive bar 826 can be more flexible with respect to height 857, i.e., in the upward and downward directions, than with respect to width 859. In at least one embodiment, width 859 can be approximately 0.12" and height 857 can be approximately 0.05". Although drive bar 826 is illustrated as having a rectangular cross-section, the invention is not so limited. On the contrary, the cross-section of drive bar 826 can include various embodiments in which the width of the drive bar cross-section is greater than its height. In at least one embodiment, drive bar 826 can include a cross-section defined by a width and a height wherein the width is greater than the height, and wherein the width defines an axis that is not parallel to an axis defined by cutting edge 124 of cutting member 120. In various embodiments, as known in the art, cutting edge 124 can include a knife edge or a wire configured to conduct current therethrough. Furthermore, in various embodiments, the drive bar can be asymmetric with respect to centerline 224 of the distal end of shaft 116, for example. In these embodiments, as a result, drive bar 826 can be predisposed to bending in a pre-determined direction.

Similar to drive bar 226, drive bar 826 can be comprised of one material or, alternatively, several layers of material bonded together. As above, the flexibility of drive bar 826 can be pre-determined by the types of materials used and the arrangement of the layers within the drive bar. Referring to FIG. 41, cutting member body 822 can include slot 869 which is configured to receive the distal end of drive bar 826. In the present embodiment, slot 869 is configured to receive drive bar 826 in a press-fit relationship, however, other means, such as adhesive or fasteners, can be used to secure drive bar 826 to cutting member 820. Similar to the above, staple cartridge 812 can include a slot configured to receive and support drive bar 826 when it enters into staple cartridge 812. In various embodiments, although not illustrated, anvil 834 could be configured to receive and support drive bar 826.

As described above, the jaws of an endocutter can be placed on opposite sides of several layers of tissue, for example, and then closed onto the tissue. In the illustrated embodiments, referring to FIG. 4, jaw 108 can be pivoted between opened and closed positions with respect to jaw 110 via the interaction of inner portion 114 and outer sleeve 116 of shaft 106 in a known manner. Although not illustrated, jaw 108 is connected to jaw 110 via a pivot connection such that when inner portion 114 moves jaw 108 relative to outer sleeve 116, jaw 108 is pivoted toward jaw 110. Throughout the movement of jaw 108, the proximal portion of jaw 108, i.e., proximal portion 111, is positioned closer to jaw 110 than its distal portion, i.e., distal portion 113, until jaw 108 is brought into its final position opposite staple cartridge 112. In this final, closed position, distal portion 113 and proximal portion 111 can be substantially equidistant from staple cartridge 112. However, as a result of distal portion 113 being the last portion of jaw 108 to reach its final position, a portion of the tissue, or an artery, for example, can escape from between jaws 108 and 110 before distal portion 113 is moved into its final position. Accordingly, the surgeon may have to reopen the jaws and reposition the end-effector in an attempt to properly capture the tissue, or artery, therebetween.

As detailed below, an end-effector in accordance with an embodiment of the present invention can be configured to capture the tissue, or an artery, between the distal and proximal portions of the end-effector before the jaws are moved into their final position. In at least one embodiment, referring to FIGS. 27-34, jaw 608 can be pivotally connected to jaw 610 via pivot connection 609. Pivot connection 609 can include first trunnion 615 and second trunnion 617 extending from jaw 608, and, in addition, first slot 619 and second slot 621 in jaw 610. Trunnions 615 and 617 can be sized and configured to fit within slots 619 and 621, respectively, such that pivot connection 609 allows for relative rotational and translation movement between jaw 608 and jaw 610. In other alternative embodiments, jaw 608 may include slots 619 and 621 and jaw 610 may include trunnions 615 and 617, or any other combination thereof.

Figure 27:
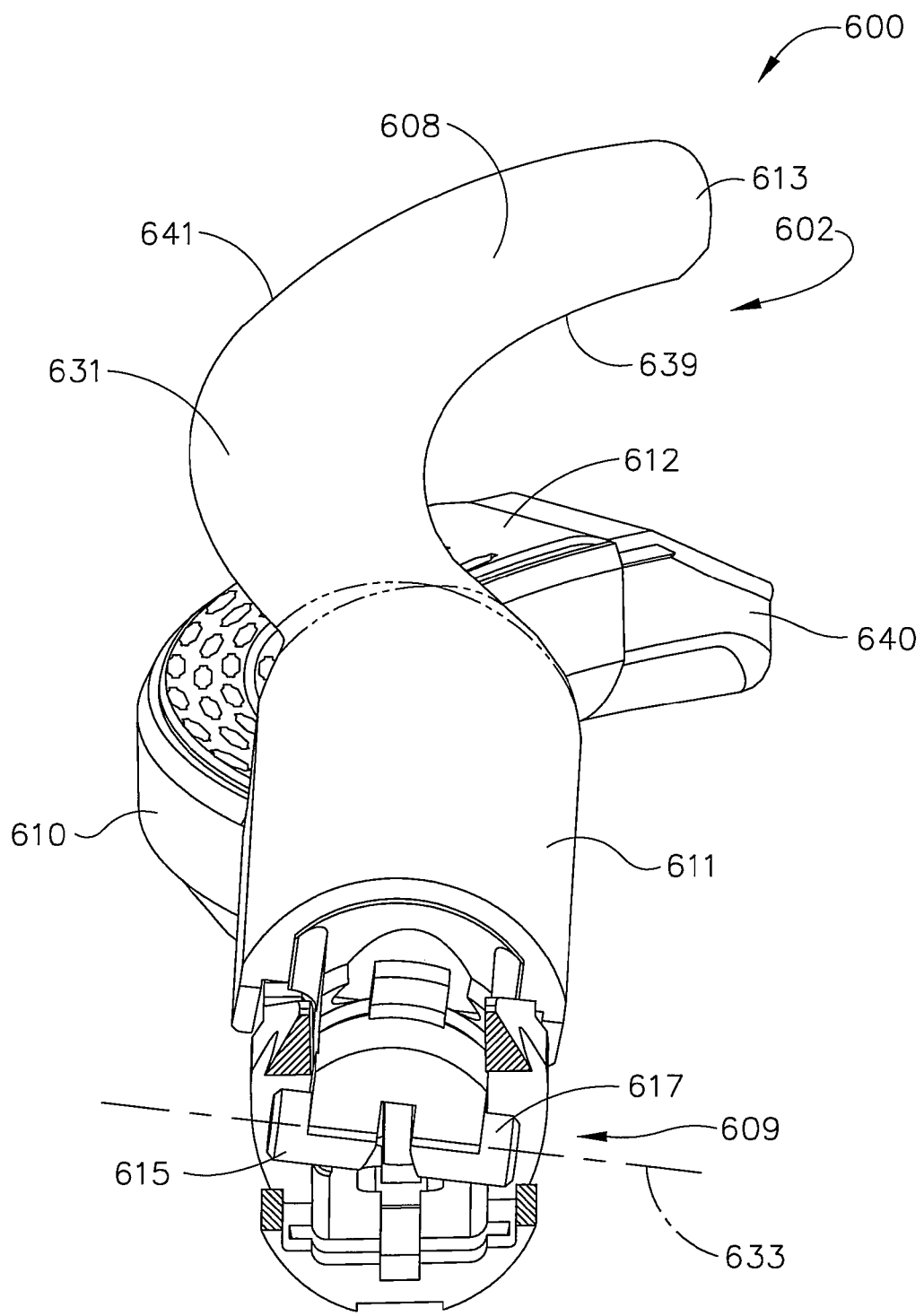
FIG. 27 is a perspective view of an endocutter having a curved end-effector configured to close in an asymmetric manner in accordance with an embodiment of the present invention.
Figure 28:
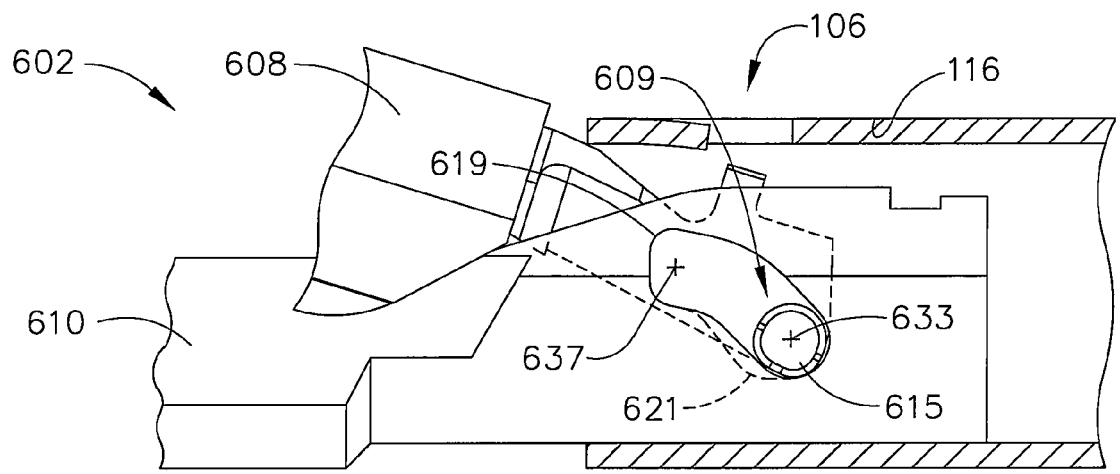
FIG. 28 is a cross-sectional view of the hinge connection between the jaws of the curved end-effector of FIG. 27 wherein the jaws are in an open configuration.
Figure 29:
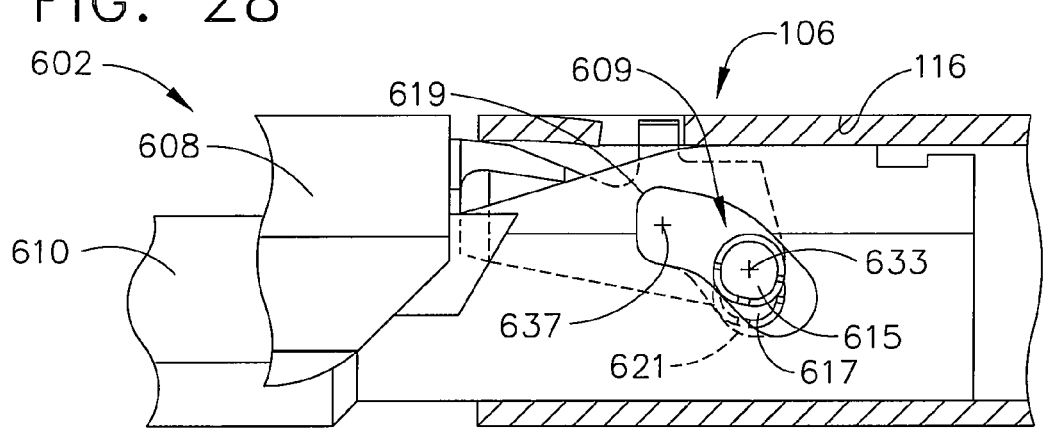
FIG. 29 is a cross-sectional view of the hinge connection of FIG. 28 wherein the jaws are in a partially closed configuration.
Figure 31:
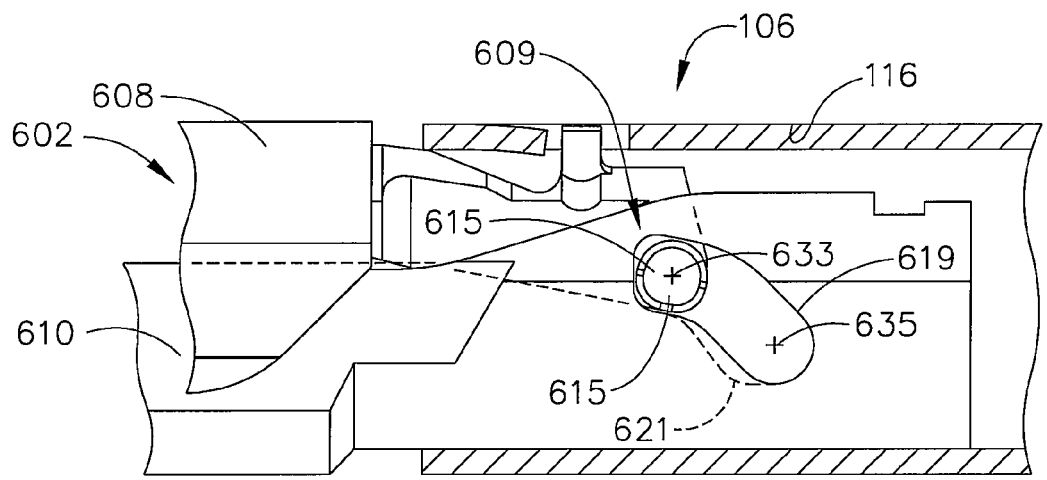
FIG. 31 is a cross-sectional view of the hinge connection of FIG. 28 wherein the end-effector is in a closed configuration.
Figure 30:
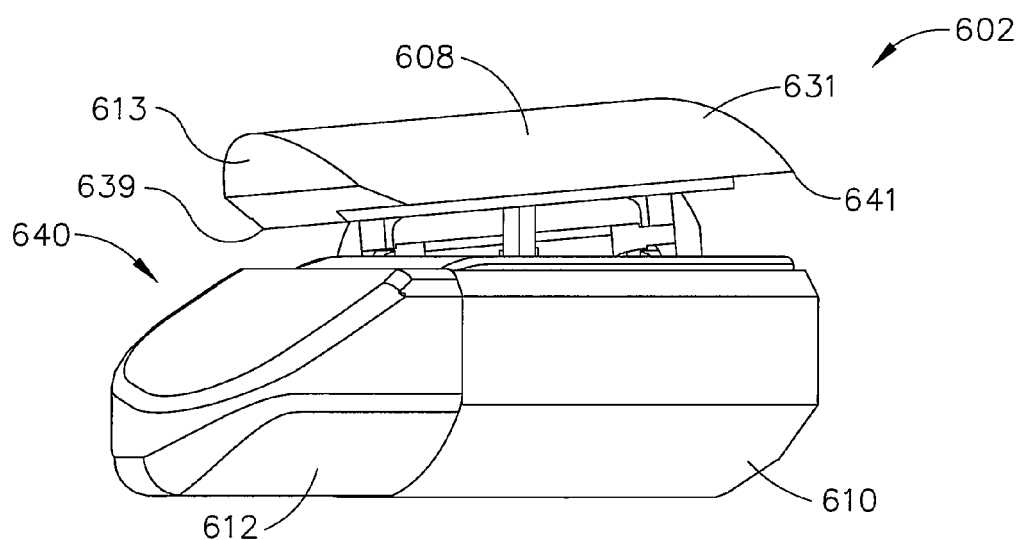
FIG. 30 is an end view of the curved end-effector of FIG. 27 illustrated in a partially closed configuration.

Referring to FIGS. 28, 29 and 31 which schematically illustrate slot 619 in solid and slot 621 in dashes, trunnions 615 and 617 are configured to travel within slots 619 and 621, respectively, and define the relative movement between jaws 608 and 610. In the present embodiment, slots 619 and 621 define two different arcuate paths for trunnions 615 and 617. More particularly, referring to FIGS. 33 and 34, slot 619 includes first portion 623, second portion 625, and intermediate portion 627 extending therebetween wherein slot 621 also includes first portion 623 and second portion 625, however, slot 621 includes an intermediate portion, i.e., portion 629, which is different than intermediate portion 627. Referring to FIG. 27, as a result of slots 619 and 621 having different intermediate portions, slots 619 and 621 can cause jaw 608 to tilt, or otherwise move in a non-symmetrical manner, with respect to jaw 610 as it is opened and closed. Advantageously, referring to FIGS. 30 and 32, such an asymmetric motion, or tilting, can allow distal portion 613 of jaw 608 to be placed in close proximity to staple cartridge 612 before the intermediate portion of jaw 608, i.e., portion 631, is moved into its final position illustrated in FIG. 32. As a result, referring to FIG. 30, an end-effector in accordance with the above can be used to capture tissue, or an artery, between proximal end 611 and distal end 613 before intermediate portion 631 is moved into its final, or closed, position. As a result, the possibility of a portion of the tissue, or artery, escaping from between jaws 608 and 610 is reduced. In addition to the above, the distal ends of jaws 608 and 610 can be brought into close opposition to each other in order to grip delicate tissue, for example, without having to completely close the end-effector.

As outlined above, slots 619 and 621 can define different paths for trunnions 615 and 617, respectively, when jaw 608 is moved between an open and a closed position. When jaw 608 is in its open position, referring to FIG. 28, trunnions 615 and 617 are positioned within first portions 623 of slots 619 and 621. In this position, axis 633, which is defined by trunnions 615 and 617, is substantially collinear with axis 635 defined between first portions 623 of slots 619 and 621. Thereafter, jaw 608 can be moved distally such that trunnions 615 and 617 move upward through slots 619 and 621. Owing to the asymmetric configurations of slots 619 and 621, referring to FIG. 27 which illustrates jaw 108 in a partially closed position, trunnion 615 is elevated to a relatively higher position with respect to trunnion 617, as evidenced by the tilting of axis 633. In this position, an inner edge of jaw 608, i.e., edge 639, can be in closer proximity to staple cartridge 612 than an outer edge of jaw 608, i.e., edge 641. Advantageously, as a result, inner edge 639 can be brought into contact against the tissue, or an artery, for example, allowing the surgeon to evaluate the position of the end-effector with respect to the tissue, or artery, without having to bring the entire anvil 634 of jaw 608 against the tissue. This feature may be particularly advantageous when the end-effector is positioned around a pulmonary artery as pulmonary arteries are especially susceptible to rupture.

Figure 32:
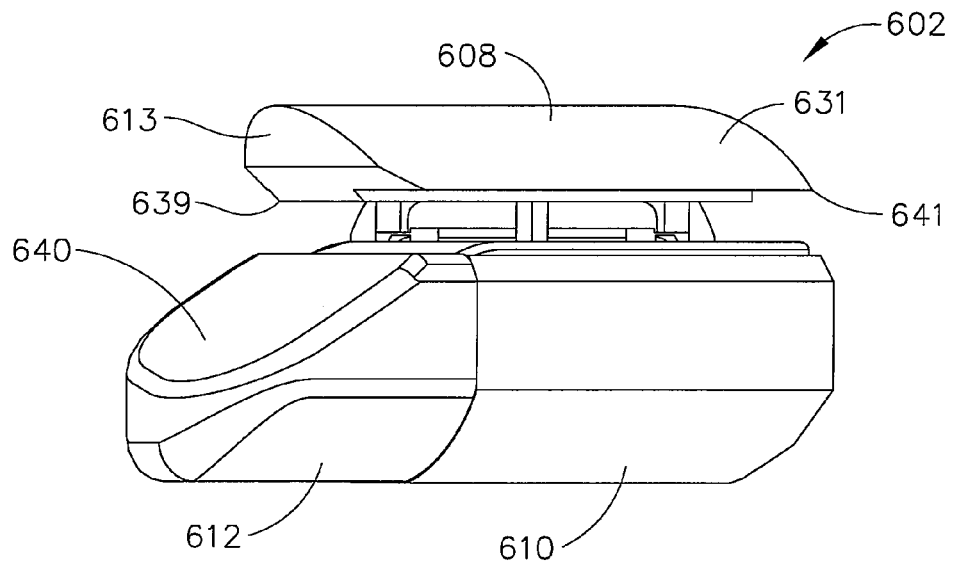
FIG. 32 is an end view of the curved end-effector of FIG. 27 illustrated in a closed configuration.
Figure 33:
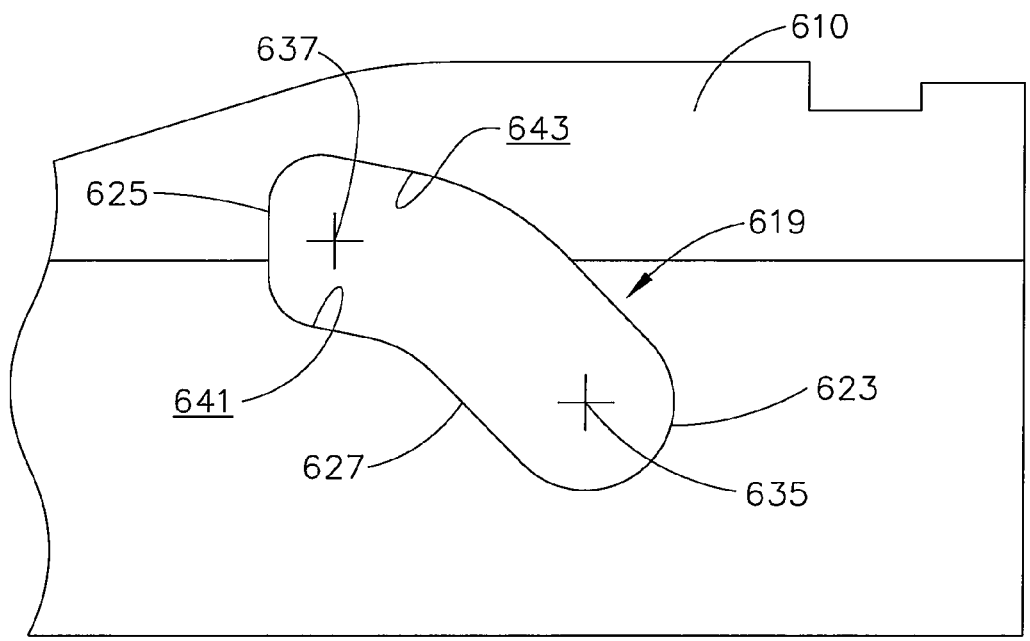
FIG. 33 is a detail view of a first slot of the hinge connection of FIG. 28 that is configured to receive a first projection extending from the anvil and is also configured to define a first path for relative movement therebetween.
Figure 34:
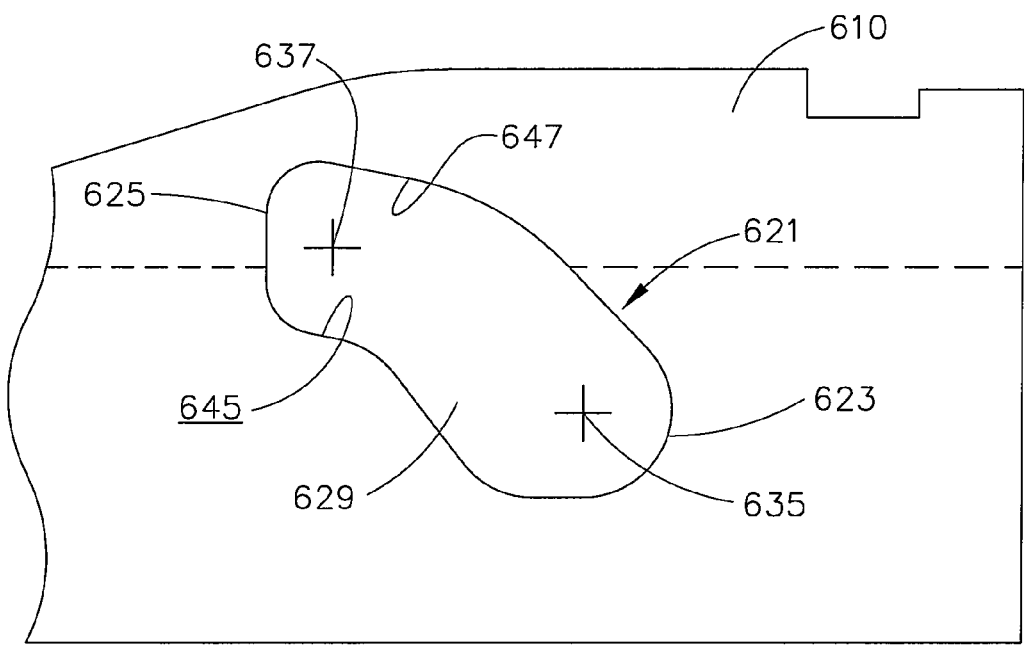
FIG. 34 is a detail view of a second slot of the hinge connection of FIG. 28 that is configured to receive a second projection extending from the anvil and is also configured to define a path for relative movement therebetween that is different than the first path.

After the tissue, or artery, has been captured between the proximal and distal ends of the end-effector, referring to FIGS. 31 and 32, jaw 608 can be moved into its final, or closed, position with respect to staple cartridge 612. In this position, axis 633, which is defined by trunnions 615 and 617, can be substantially collinear with axis 637 defined between second portions 625 of slots 619 and 621. Furthermore, in this final position, intermediate portion 631, distal portion 613 and proximal portion 611 can be equidistant from staple cartridge 612. Similarly, outer edge 641 and inner edge 639 can also be positioned equidistant with respect to staple cartridge 612. In this final position, tissue, or an artery, for example, can be securely retained between jaws 608 and 610. Although the above-described embodiments include a curved end-effector, the invention is not so limited. On the contrary, the above features can be utilized with a linear end-effector, for example, to achieve the advantages described above.

In various embodiments, slots 619 and 621 can define paths having different centerlines wherein each centerline can be defined as the line equidistant from the top and bottom surfaces of each slot. For example, referring to FIGS. 33 and 34, slot 619 can include bottom surface 641 and top surface 643 which define a centerline therebetween that is different than the centerline defined by bottom surface 645 and top surface 647 of slot 621. In these embodiments, slots 619 and 621 can be configured to closely retain trunnions 615 and 617 between these top and bottom surfaces such that axis 633 of trunnions 615 and 617 substantially travels along the centerlines of slots 619 and 621. In various embodiments, jaws 608 and 610 can be configured such that trunnions 615 and 617 contact bottom surfaces 641 and 645 of slots 619 and 621. In these embodiments, jaw 608 can be biased by a spring, for example, such that trunnions 615 and 617 are positioned against bottom surfaces 641 and 645 throughout the movement of jaw 608. Owing to different profiles for bottom surfaces 641 and 645, the advantages described above can be achieved.

As described above, once the jaws of the end-effector are closed onto the layers of tissue, for example, staples can be deployed into the tissue. However, oftentimes, the layers of tissue are very thin and the staples may not properly capture the tissue therein. To ameliorate this problem, as known in the art, buttress material can be placed on one or both sides of the tissue to support the tissue as it is being stapled. In such embodiments, the purchase of the staples is improved and the clamping force of the staples may be spread more evenly across the buttress material. In various embodiments, the buttress material can be comprised of a bioabsorbable material such that it can dissolve away during the healing process. Previously, however, the buttress material has been provided in linear strips which are configured to accommodate linear staple lines and end-effectors. Such linear strips may be unsuitable for use with endocutters having a curved end-effector configured to deploy staples in curved staple lines.

Figure 47:
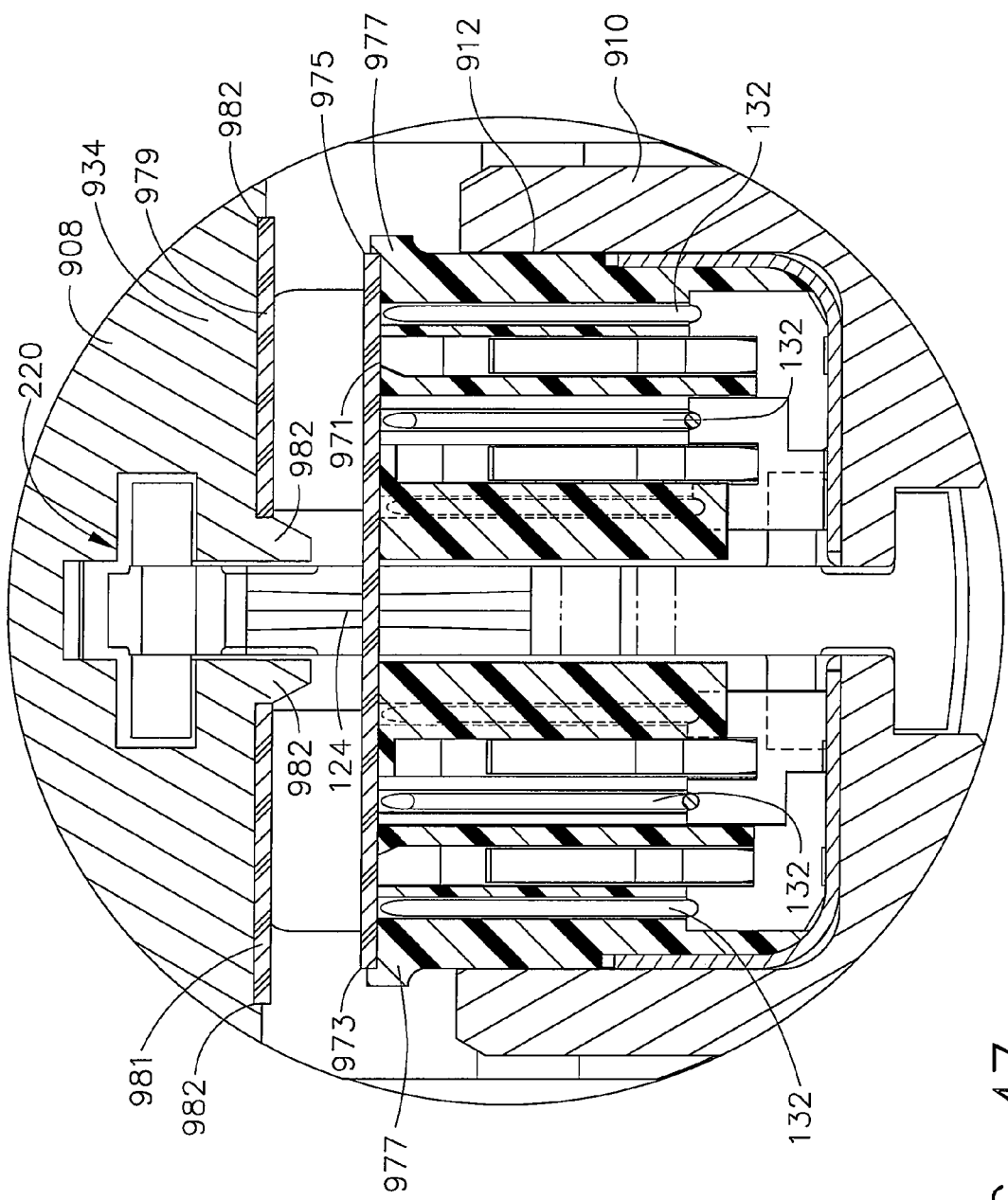
FIG. 47 is a cross-sectional view of the end-effector of the endocutter of FIG. 44 taken along line 47-47 in FIG. 44.

In accordance with an embodiment of the present invention, referring to FIGS. 44-47, curved staple cartridge 912 can be configured to receive a curved piece, or pieces, of buttress material thereon, such as buttress material 971. Curved buttress material 971 can include inner edge 973 which can be configured to substantially parallel the inner radius of curvature of jaw 910, and, in addition, outer edge 975 which can be configured to substantially parallel the outer radius of curvature of jaw 910. In some embodiments, referring to FIG. 47, staple cartridge 912 can include lip 977 extending therefrom which is configured to retain buttress material 971 on staple cartridge 912. More particularly, lip 977, as illustrated, can be configured to limit lateral movement of buttress material 971 with respect to staple cartridge 912 and, although not illustrated, lip 977 can also be configured to extend distal to and/or proximal to the ends of the buttress material to limit relative axial movement between buttress material 977 and staple cartridge 912. Similar to the above, curved anvil 934 can be configured to receive a piece, or pieces, of curved buttress material thereon, such as buttress material 979 and 981, for example. Referring to FIG. 47, anvil 934 can include several lips 982 which are configured to limit relative movement between buttress material 979 and 981 and anvil 934. In various embodiments, an adhesive, such as cyanoacrilate, for example, can be applied to the buttress material, anvil and/or staple cartridge to further limit the movement of the buttress material or otherwise prevent the mobilization thereof.

As a result of the above, a surgeon may be able to position the end-effector into a surgical site without the buttress material falling off or moving relative to the staple cartridge and/or anvil. Once positioned, cutting member 120 can be advanced to cut buttress material 971. More specifically, referring to FIG. 47, cutting edge 924 can be aligned with buttress material 971 such that it cuts the buttress material as cutting member 920 is advanced through staple cartridge 912. However, in some circumstances, the cutting member may at least partially dislodge the buttress material relative to the staple cartridge. This relative movement may especially occur when the buttress material is thick, or, the cutting member must cut more than one piece of buttress material at a time. To ameliorate this problem, the buttress material may include a series of perforations, for example, positioned along the path in which the cutting member will cut the buttress material. In these embodiments, these perforations may be formed along a radius of curvature which is parallel to and positioned intermediate two curved staple rows. In other various embodiments, the buttress material may include other features which disrupt the cross-sectional thickness of the buttress material to facilitate the cutting of the buttress material. As a result of the above, less force may be required to cut the buttress material and, accordingly, it is less likely the buttress material may slide, for example, when it is cut.

Figure 48:
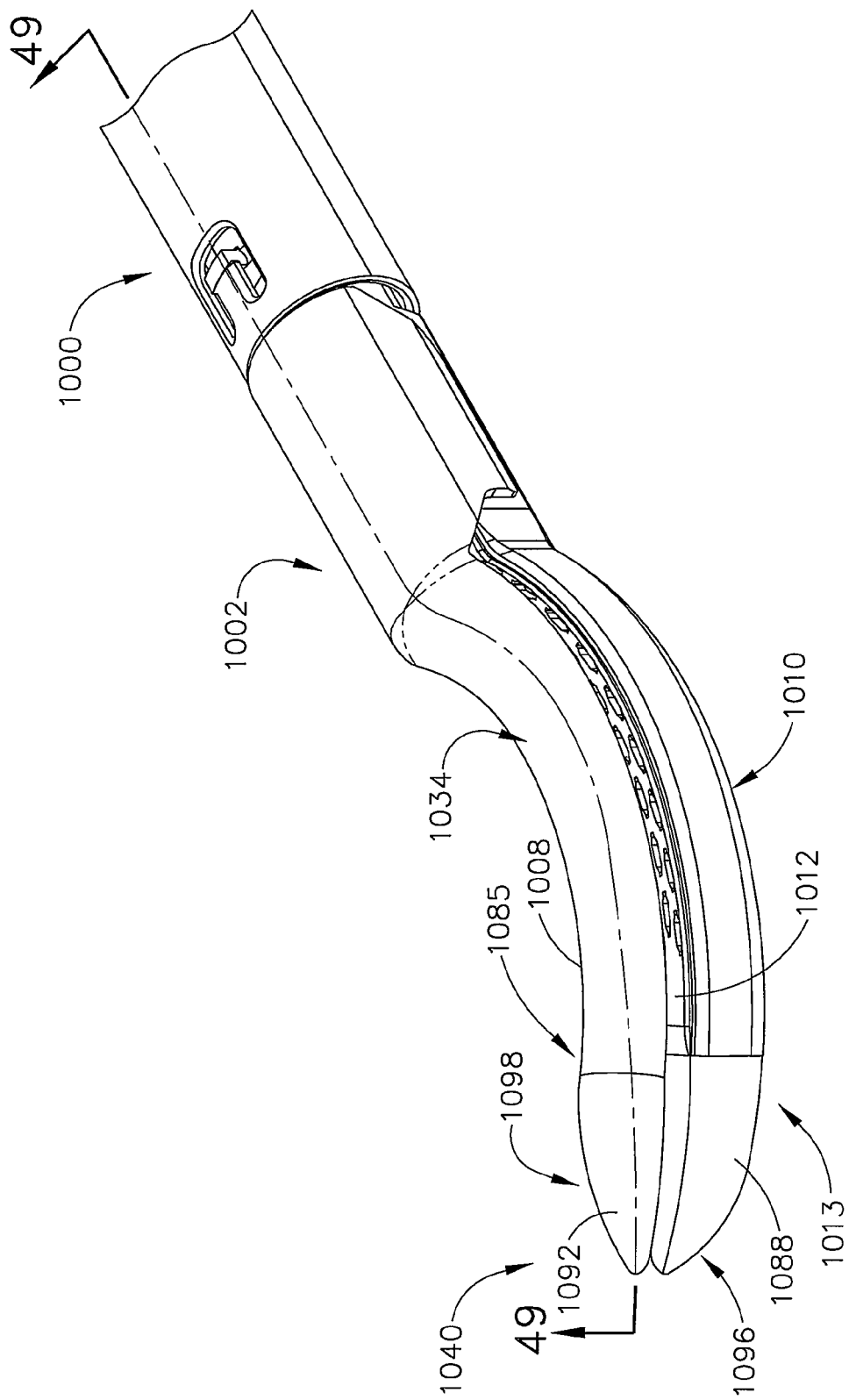
FIG. 48 is a perspective view of an endocutter in accordance with an embodiment of the present invention.

FIGS. 48-50 illustrate another surgical instrument of the present invention. As can be seen in these Figures, the surgical instrument 1000 includes an end-effector 1002 that has a first jaw 1008 and a second jaw 1010. The second jaw 1010 may comprise a channel 1038 that is configured to operably support a staple cartridge 1012 therein. Staple cartridge 1012 may be removably supported in the channel 1038 or, in various embodiments, staple cartridge 1012 may form an integral part of the second jaw 1010. The surgical instrument 1000 further includes a movable anvil 1034 that may be movably coupled to the lower jaw 1010 in the various manners described above or in other manners that are known in the art.

In the embodiment depicted in FIGS. 48-50, the end effector 1002 has a distal end generally designated as 1040. As can further be seen in those Figures, the staple cartridge 1012 has a blunt first tip portion 1088 thereon. The first tip portion 1088 may be integrally formed (molded, machined, etc.) on the distal end 1013 of the staple cartridge 1012 or it may comprise a separate piece that may be formed with a cavity 1089 (FIG. 50) configured to receive a nose 1083 of a conventional staple cartridge 1012. The first tip portion 1088 can include snap features 1090 (FIG. 50) or other suitable retainer portions formed therein to retainingly mate with complementary retention grooves 1084 formed in the nose 1083. In addition, or in the alternative, the first tip portion 1088 may be affixed to the cartridge 1012 by adhesive such as, for example, cyanoacrylates, light-curable acrylics, polyurethanes, silicones, epoxies, and ultra-violet curable adhesives such as Henkel Loctite®. In other embodiments, a combination of snap features and grooves may be provided in both the staple cartridge 1012 and the first tip portion 1088. Still other forms of fasteners and fastener arrangements may be used to affix the first tip portion 1088 to the staple cartridge 1012. In other embodiments, the first tip portion 1088 may be affixed to the channel 1038. As can be seen in FIG. 50, the first tip portion 1088 has a first upwardly extending curved outer surface.

Similarly, in this embodiment, the anvil 1034 may be equipped with a second tip portion 1092. The second tip portion 1092 may be integrally formed (molded, machined, etc.) on the distal end 1085 of the anvil 1034 or it may comprise a separate piece that may be formed with a cavity 1093 configured to receive an end portion of a conventional anvil 1034 with snap features 1094 or other suitable retainer portions formed therein to retainingly mate with complementary retention grooves 1086 formed in distal end 1085. In addition, or in the alternative, the second tip portion 1092 may be affixed to the anvil 1034 by adhesive such as, for example, cyanoacrylates, light-curable acrylics, polyurethanes, silicones, epoxies, and ultra-violet curable adhesives such as Henkel Loctite®. In other embodiments, a combination of snap features and grooves may be provided in both distal end 1085 and the second tip portion 1092. Still other forms of fasteners may be used to affix the second tip portion 1092 to the anvil 1034. As can be seen in FIG. 50, the second tip portion 1092 has a downwardly extending substantially curved outer surface.

In various embodiments, the first tip portion 1088 and the second tip portion 1092 may be fabricated from a variety of different materials that may be identical to or different from the materials from which the staple cartridge 1012 and anvil 1034 are manufactured. For example, the first tip portion 1088 and the second tip portion 1092 may be manufactured from soft plastic, rubber, etc. The first tip portion 1088 and the second tip portion 1092 may be fabricated from the same or different materials.

In various embodiments, the first tip portion 1088 and the second tip portion 1092 are shaped such that their respective outer surfaces 1088', 1092' cooperate to substantially form a substantially blunt end effector nose generally designated as 1096 that, in one exemplary embodiment, has a paraboloid surface 1098 when the anvil 1034 is in the closed position as shown in FIG. 50. As used herein, the term "paraboloid surface" means a surface having parabolic sections parallel to a single coordinate axis and elliptic sections perpendicular to that axis. Those of ordinary skill in the art will appreciate that when employing various embodiments of the instrument 1000, as long as the surgeon can see one or the other of the first tip portion or second tip portion, the surgeon will know where the other tip portion is, even if it is behind tissue or other structures. In addition, the unique and novel tip configurations permit the surgeon to pass the anvil and/or channel around tissue without great risk of incidental trauma to adjacent tissues. Furthermore, when in the closed orientation as depicted in FIGS. 49 and 50, these embodiments are particularly well suited for use as a dissector for separating and manipulating tissues.

The first tip portion and the second tip portion have been described and depicted in the Figures as being used in connection with a curved end effector. Those of ordinary skill in the art will readily appreciate, however, that the first and second tip portions may be used in connection with a variety of different end effector configurations such as linear endocutters and other types of end effectors without departing from the spirit and scope of the present invention. Thus, the first and second tip portions described above should not be limited solely to use in connection with curved endocutters/staplers.

As was described above, the first tip portion may be constructed for attachment to the distal end of a conventional staple cartridge or it may be integrally formed on the end of the staple cartridge. In still other embodiments, the first tip portion may be constructed for attachment to a distal end of the channel or it may be integrally formed on the distal end of the channel. Similarly, the second tip portion may be constructed for attachment to a conventional endocutter anvil or it may be integrally formed on the distal end of the anvil. In those applications wherein the first tip portion and/or second tip portion are fabricated separately from the cartridge and anvil, respectively, the tip portions may be supplied as a kit for retrofitting onto the cartridge and anvil by the end user. For example, in such arrangements, the tip portions may be presterilized and packaged and be configured to snap onto or otherwise attach to the staple cartridge and anvil or channel and anvil, whichever the case may be.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A surgical stapler for stapling tissue, comprising:
   a channel configured for receiving a staple cartridge, the staple cartridge configured to removably store staples therein;
   an anvil configured to deform the staples, said anvil having a proximal portion, a distal portion, and a middle portion intermediate said proximal portion and said distal portion, wherein said anvil is movable between a first position and a second position, wherein said anvil and the staple cartridge are configured to hold said tissue therebetween when said anvil is in said second position, and wherein said proximal portion and said distal portion of said anvil are closer to the staple cartridge than said middle portion when said anvil is in said second position; and
   a hinge connecting said anvil to said channel, wherein said hinge is configured to permit said anvil to pivot toward said channel, and wherein said hinge is configured to permit said anvil to tilt relative to said channel.

2. The surgical stapler of claim 1, wherein said middle portion of said anvil is closer to the staple cartridge than said distal portion when said anvil is in said first position.

3. The surgical stapler of claim 1, wherein said anvil is movable between said second position and a third position, wherein said proximal portion, said middle portion and said distal portion are substantially equidistant from the staple cartridge when said anvil is in said third position.

4. The surgical stapler of claim 1, further comprising a handle portion and a shaft, wherein said shaft extends between said handle portion and said staple cartridge channel, wherein said shaft defines an axis, and wherein said anvil and the staple cartridge are configured to deploy at least two curved rows of staples with respect to said axis.

5. The surgical stapler of claim 1, wherein said anvil further includes a first edge extending between said proximal portion and said distal portion and a second edge extending between said proximal portion and said distal portion, and wherein said first edge is closer to the staple cartridge than said second edge when said anvil is in said second position.

6. The surgical stapler of claim 5, wherein said first edge and said second edge are substantially equidistant from the staple cartridge when said anvil is in said first position.

7. The surgical stapler of claim 5, wherein said first edge is defined by a first radius of curvature, wherein said second edge is defined by a second radius of curvature, and wherein said second radius of curvature is greater than said first radius of curvature.

8. The surgical stapler of claim 5, wherein said anvil is movable between said second position and a third position, and wherein said first edge and said second edge are substantially equidistant from the staple cartridge when said anvil is in said third position.

9. The surgical stapler of claim 1, further comprising said staple cartridge.

10. A surgical stapler for stapling tissue, comprising:
    a channel configured for receiving a staple cartridge, the staple cartridge configured to removably store staples therein;
    an anvil configured to deform the staples, said anvil having a proximal portion, a distal portion, and a middle portion intermediate said proximal portion and said distal portion, wherein said anvil is movable between an open position, a partially-closed position, and a closed position, wherein said anvil and the staple cartridge are configured to hold the tissue therebetween when said anvil is in said partially-closed position, and wherein said proximal portion and said distal portion of said anvil are closer to the staple cartridge than said middle portion when said anvil is in said partially-closed position; and
    a hinge connecting said anvil to said channel, wherein said hinge is configured to permit said anvil to pivot toward said channel, and wherein said hinge is configured to permit said anvil to tilt relative to said channel.

11. The surgical stapler of claim 10, wherein said middle portion of said anvil is closer to the staple cartridge than said distal portion when said anvil is in said open position.

12. The surgical stapler of claim 10, wherein said proximal portion, said middle portion and said distal portion are substantially equidistant from the staple cartridge when said anvil is in said closed position.

13. The surgical stapler of claim 10, further comprising a handle portion and a shaft, wherein said shaft extends between said handle portion and said staple cartridge channel, wherein said shaft defines an axis, and wherein said anvil and the staple cartridge are configured to deploy at least two curved rows of staples with respect to said axis.

14. The surgical stapler of claim 10, further comprising said staple cartridge.

15. A surgical stapler for stapling tissue, comprising:
    a channel configured for receiving a staple cartridge, the staple cartridge configured to removably store staples therein;
    an anvil configured to deform the staples, said anvil having a proximal portion, a distal portion, and a middle portion intermediate said proximal portion and said distal portion, wherein said anvil is movable between an open position, a partially-closed position, and a closed position, wherein said anvil and the staple cartridge are movably connected such that, when said anvil is in said partially-closed position, said middle portion and said staple cartridge are separated by a first distance and said distal portion and said staple cartridge are separated by a second distance, wherein said first distance is greater than said second distance; and
    a hinge connecting said anvil to said channel, wherein said hinge is configured to permit said anvil to pivot toward said channel, and wherein said hinge is configured to permit said anvil to tilt relative to said channel.

16. The surgical stapler of claim 15, wherein said second distance is greater than said first distance when said anvil is in said open position.

17. The surgical stapler of claim 15, wherein said first distance and said second distance are substantially equal when said anvil is in said closed position.

18. The surgical stapler of claim 15, further comprising a handle portion and a shaft, wherein said shaft extends between said handle portion and said staple cartridge channel, wherein said shaft defines an axis, and wherein said anvil and the staple cartridge are configured to deploy at least two curved rows of staples with respect to said axis.

19. The surgical stapler of claim 15, further comprising said staple cartridge.

* * * * *